United States Patent [19]
Samarut et al.

[11] Patent Number: 4,957,865
[45] Date of Patent: Sep. 18, 1990

[54] CLONING OR EXPRESSION VECTORS CONTAINING THE AVIAN ERYTHROBLASTOSIS VIRUS GENOME AND CELLS TRANSFECTED BY THESE VECTORS

[75] Inventors: Jacques Samarut, Villeurbanne; Gérard Verdier, Fontaines S/Saone; Miloud Benchaibi, Villeurbanne; Pierre Savatier, Lyon; Didier Poncet, Lyon; Frédéric Flamant, Lyon; Jiao-Hao Xiao, Strasbourg Cedex; Pierrick Thoraval, Villeurbanne; Frédérique Chambonnet, Saint.Etienne; Victor Nigon, Villeurbanne, all of France

[73] Assignee: Institut National de la Recherche Agronomique (INRA), Paris, France

[21] Appl. No.: 879,103
[22] PCT Filed: Oct. 15, 1985
[86] PCT No.: PCT/FR85/00293
 § 371 Date: Jun. 4, 1986
 § 102(e) Date: Jun. 4, 1986
[87] PCT Pub. No.: WO86/02380
 PCT Pub. Date: Apr. 24, 1986

[30] Foreign Application Priority Data
 Oct. 15, 1984 [FR] France ............... 84 15764

[51] Int. Cl.$^5$ ............ C12N 7/00; C12N 15/00; C12P 21/00
[52] U.S. Cl. ............ 435/235; 435/320; 435/317.1; 435/69.1; 935/32; 935/57
[58] Field of Search ............ 435/235, 320, 68; 935/32

[56] References Cited
U.S. PATENT DOCUMENTS
 4,405,712 9/1983 Vande Woude et al. ......... 435/5
 4,686,098 8/1987 Kopchick et al. ............ 424/524

FOREIGN PATENT DOCUMENTS
 0105141 8/1983 European Pat. Off. .
 0155198 1/1985 European Pat. Off. .

OTHER PUBLICATIONS
Shuman, Poultry Science 65: 1437–44 (1986).
Sealy et al. (b), *Virology* 130: 155–194.
Frykberg et al., *Cell* 32: 227–238 (1983).
Doehmer et al., *Proc. Nat. Acad. Sci. U.S.A.* 79: 2268–2272 (1982).
Crittenden et al., Avian Diseases 30(1): 43–46 (1986).
Mulligan, In "Expt. Manipulation of Gene Expression", ed. by Inouye, pp. 155–173, Chapter 8 (1983) Academic Press, New York.
Miller et al., *Proc. Natl. Acad. Sci. U.S.A.* 80: 4709–4713 (1983).
Vennström et al., *J. Virology* 36: 575–585 (1980).
Sorge et al., J. Mol. Appl. Genetics I: 547–559 (1982).

*Primary Examiner*—Charles F. Warren
*Assistant Examiner*—Jasmine C. Chambers
*Attorney, Agent, or Firm*—Bertram I. Rowland

[57] ABSTRACT

The invention relates to a virus for cloning or expression of a foreign gene, characterized in that it consists of all or part of the genome of avian erythroblastosis virus and contains at least one foreign gene situated between the 3 LTR sequences.

19 Claims, 27 Drawing Sheets

FIG_7

FIG_11

FIG_12

FIG_13

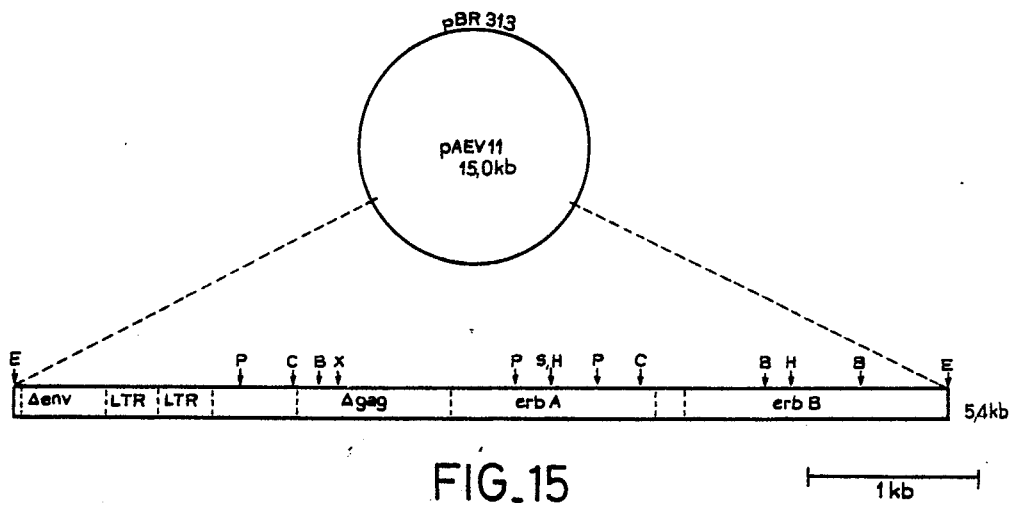
FIG_15
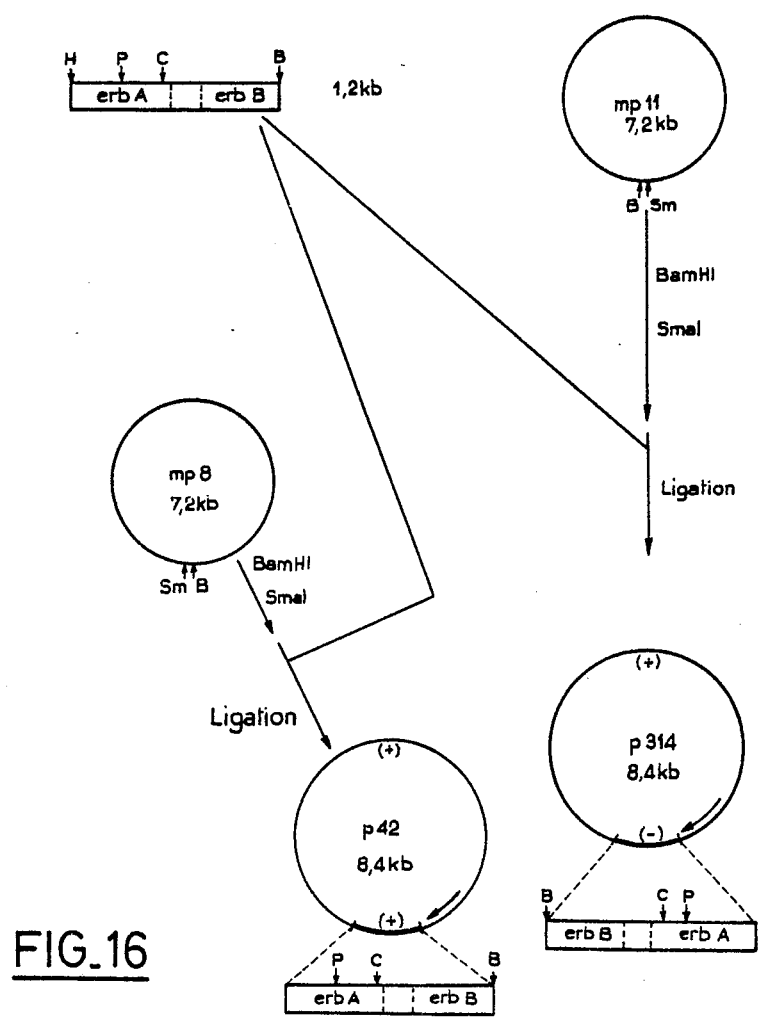
FIG_16

```
AEV-H 5'-AUG ——— CCA AAT GGC TCC AAA ACT CCA TCT ATC GCG GCT GGT
AEV   5'-AUG ——— --- --- --- --- --- --- --- --- --- --- --- ---
             GTT GTC GGA GGA CTC CTG TGC CTG GTT GTG GTT GGT
             --- --- --- --- --- --- --- --- --- --- --- ---
             CTA GGC ATC GGT CTT TAC CTG CGG CGA CGT CAT ATC
             --- --- --- --- --- --- --- --- --- --C --- ---
             GTG CGG AAG CGC ACC CTG CGC AGG CTG CTG CAA GAG
             --- --- --- --- --- --- --- --- --- --- --- ---
             AGG GAG CTT GTC GAA CCA CTG ACA CCC AGT GGG GAG
             --- --- --- --- --- --- --- --- --- --- --- ---
             GCA CCA AAC CAG GCC CAC CTG AGA ATT TTA AAG GAA
             --- --- --- --- --- --- --- --- --- --- --- ---
             ACA GAA TTT AAA AAG GTC AAA GTT TTG GGC TCT GGA
             --- --- --- --- --- --- --- --- --- --- -T- ---
             GCT TTT GGC ACT ATT TAT AAG GGA CTT TGG ATC  AEV-H
             --- --- --- --- G-- --- --- --- --- --- ---  AEV
                                                    ——C
                                                    BamHI
```

FIG.17

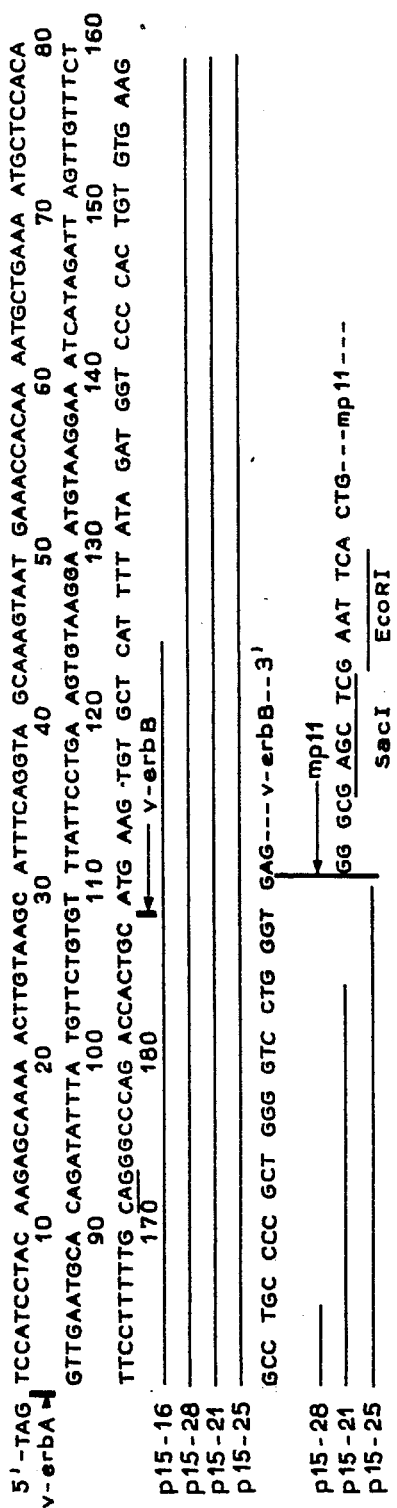
FIG._18

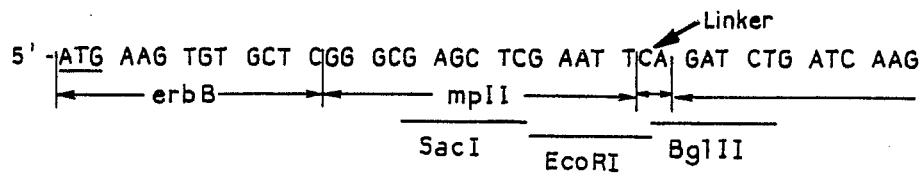
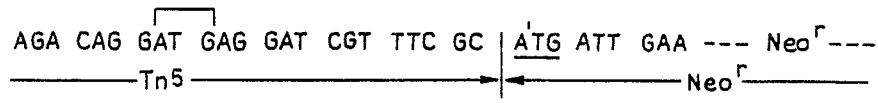
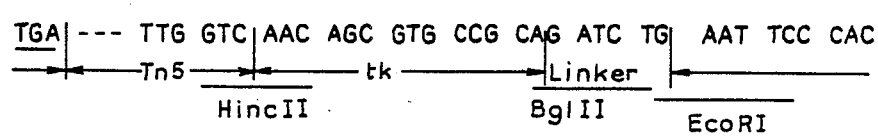
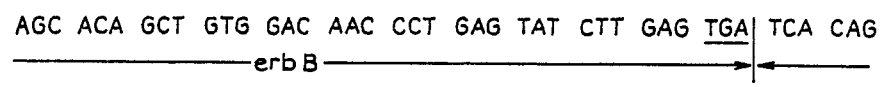
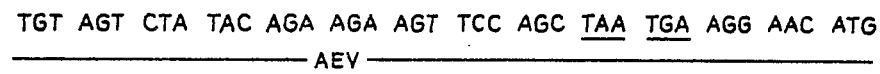
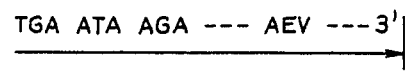
FIG. 22

FIG._27

CLONING OR EXPRESSION VECTORS CONTAINING THE AVIAN ERYTHROBLASTOSIS VIRUS GENOME AND CELLS TRANSFECTED BY THESE VECTORS

The stable introduction of genetic material into organisms generally involves the accomplishment of this transfer in precursor cells having high potentialities for multiplication and differentiation. These precursor cells can either be representative of a very special differentiation pathway, such as, for example, cells of haematopoietic origin, or they can be totipotent such as germ cells. In all cases, the population of target cells for the transfer is in a tiny minority in the tissues in question.

The stable introduction of genetic sequences in these cells hence requires the use of transfer techniques, the yield of which should be high. Classical methods for introducing purified DNA fragments into cells in culture give rise to low levels of incorporation.

The use of compound vectors containing viral genomes have enabled a distinct improvement to be achieved in the incorporation of an exogenous sequence into a cell in culture.

The present invention relates to new vectors of this type, and especially gene transfer vectors derived from retroviruses, in particular avian erythroblastosis retrovirus.

Retroviruses owe to their special structure the capacity to be integrated readily in the form of a provirus in the genomic DNA of the cells which they infect. The structural elements which provide for this integration are carried at both ends of the provirus and are known as "long terminal repeat" or LTR.

This ease of insertion of the retroviruses within the genome of the cells which they infect has led to the idea of using them as a potential vector for transferring genetic material.

The genome of avian erythroblastosis retrovirus (AEV) contains two onc genes known as v-erbA and v-erbB, the expressions of which are responsible for the oncogenic power of this retrovirus.

In a first embodiment of the invention, the oncogenic power of the AEV virus was used as a selection marker and its capacity for insertion was used for transferring to the cells in culture an exogenous gene inserted in this retrovirus.

In a second embodiment of the invention, the oncogenic power of the AEV virus is eliminated and the marker gene is a foreign gene, for example a gene for resistance to an antibiotic such as G418.

A brief study of the characteristics of retroviruses will facilitate a better understanding of the invention.

The genome of a retrovirus which is not replication-defective (FIG. 1) is composed of an RNA molecule possessing, in the direction of the transcription (5'→3') an identical short sequence at each end, known as R (between 21 and 80 bases). This is followed, in order, by a single sequence known as U5 (from 70 to 80 bases), a tRNA binding site (TBS, approximately 20 bases), and a non-coding sequence ("leader" sequence). The RNA molecule continues with a region coding for three genes, the translation products of which are essential for the replication of the virus, and which are gag (virion structural proteins), pol (reverse polymerase) and env (envelope). The genome terminates, in order, with a non-coding sequence, a purinerich sequence (PU), a single sequence known as U3 (from 200 to 450 bases), and finally the R sequence. The repeat end sequences (R) or single sequences (U5 and U3) peculiar to retroviruses appear to be rather well conserved in this group of viruses and contain the signals involved in the control of the expression of the viral genome.

Some retroviruses, such as AEV, which are responsible for neoplastic transformations giving rise to leukaemias or tumours, owe their transforming power to the presence of special "onc" sequences in their genome. These onc sequences are cellular in origin, and have been integrated in the viral genome following recombinations with the genome of the cells which are hosts for the virus. In most of these viruses, this integration is accompanied by the complete or partial loss of gag, pol and env genes. These viruses are consequently replication-defective. In order to replicate, these viruses require the presence in the same host cell of a functional helper virus.

Helper viruses are capable of replication. Their genome only contains the functional gag, pol and env genes.

The cycle of infection by a retrovirus begins with the adsorption of the virions on the surface of the cells, followed by penetration into the cytoplasm. The stages representing the replication and viral cycle of a retrovirus are summarised in FIG. 1. In the cytoplasm of the cell, the single-stranded viral RNA (a) is transcribed by the reverse polymerase present in the virion, to a linear copy of double-stranded DNA (b). The DNA copy resulting from this reverse transcription is slightly longer than the viral RNA molecule which acted as a template for it. This difference is the result of the addition of a U3 sequence at the 5' end and a U5 sequence at the 3' end.

The combination, in order, of the U3-R-U5 sequences constitutes a repeat sequence at both ends of the DNA molecule, known as LTR (Long Terminal Repeat). The copies of viral DNA containing one or two LTR sequences are conveyed to the nucleus where they are converted to molecules of circular shape (c). Some circular molecules only retain a single LTR. These molecules are then integrated in the cell genomic DNA (d). The viral DNA is integrated in the cell DNA in such a manner that it is enclosed by an LTR at each end, and then bears the name of proviral DNA or provirus. We shall henceforward designate as "left LTR" of a provirus the LTR situated upstream of the gag gene, and as "right LTR" the LTR situated downstream of the env gene.

The provirus acts as template for the transcription of viral RNA molecules. The transcription is initiated at the R sequence of the left LTR and stops beyond the polyadenylation signal carried by the U3 or R sequence of the right LTR. The RNA molecules obtained after transcription of the provirus are a reflection of the mRNA of the eucaryotic cells, "capped" by a terminal 7mG residue at the 5' end and provided with a polyadenylated sequence at their terminal 3' end.

The RNA molecules associate to dimers by hydrogen bonds at their 5' end, and are encapsidized in the viral protein envelope. The viral particles form an assembly which sediments at 70S. They are ejected outside the cell which produces them and proceed to infect the neighbouring cells. This release of viral particles is not accompanied by the death of the cell.

The use of AEV retrovirus as a vector for cloning or expression of a foreign gene (hereinafter vector AEV)

can assume different forms as a result of its development process.

The description below refers more especially to AEV virus, but the invention generally relates to retroviruses and more especially avian retroviruses. Among retroviruses, the invention is more especially advantageous for retroviruses in which two genes can be expressed simultaneously from the same promoter, especially from the promoter present in the LTR sequences, and which depend on two genomic and subgenomic RNA molecules.

When the vector AEV is employed under conditions which enable its replication and the formation of virions to take place, that is to say with a helper virus, the infection of cell culture in vitro may be carried out with considerable efficiency, taking into account the multiplication of the infectious virions.

However, on the other hand, the integration in the form of provirus makes it possible to envisage the permanent modification of the genome of a collection of cells without the infectious nature persisting in the absence of helper virus.

The present invention hence relates to the use of avian retroviruses, especially AEV, by way of vectors for cloning or expression of a foreign gene.

Naturally, when AEV is used by way of a vector, for the requirements of producing the vector or for practical reasons of use, a portion of the genome may have been deleted or modified.

Nevertheless, reference will continue to be made to AEV, to the extent that the virus obtained will continue to retain the essential characteristics of the wild-type AEV virus, that is to say the existence of LTR sequences which provide for its integration.

The terms "vector for cloning or expression" are known in the field of genetic engineering.

Furthermore, since AEV is an RNA virus, the term "virus" may sometimes denote the viral genome in DNA form, just as in certain cases the foreign "gene" may be in RNA form, especially when it is inserted in the genome of a virion.

The techniques by which it is possible to pass from a DNA form to the RNA form and vice versa are known, being transcription and reverse transcription.

"Foreign gene" is understood to denote a gene which is not present in the natural AEV genome, and which is preferably not present in the genome of a virus.

The recombinant virus can be used as such in the form of RNA virion, but the viral genome in DNA form containing the insertion of a foreign gene, itself also in DNA form and corresponding to the reverse transcription of the RNA of the virus, can be integrated in a DNA vector such as a plasmid, cosmid or phage, for example.

The essential characteristic of these vectors is that the foreign gene is inserted between the two LTR sequences of the retrovirus, especially AEV.

The retroviruses in question are, more often than not, defective, and for this reason, when the vector in question has to be replicated, it will be used in the presence of a functional helper virus which will contain at least the missing functional genes for the replication of AEV, that is to say, in general, the gag, pol and env genes.

In general, the foreign gene or genes must hence be inserted so as to preserve the initiation and stopping of transcription, the polyA addition site in the LTR and the splicing signals.

As stated above, this type of vector may be used in two main forms, depending on the nature of the marker gene used.

Indeed, the marker gene can turn to account the oncogenic properties of AEV, thereby giving rise to oncogenic vectors which can be used more especially for cell cultures, or alternatively the oncogenic activity will have been eliminated and replaced by a marker gene for resistance to a drug similar to an antibiotic, such as G418, thereby giving rise to a non-oncogenic vector which can be used, for example, for certain "in vivo" gene transfers.

Oncogenic vectors

The AEV genome, shown schematically in FIG. 2, b consists of a "leader" sequence situated immediately downstream of the U5 region. This sequence is followed by a gag gene truncated in its 3' half. The pol gene is absent.

The onc v-erbA and v-erbB genes cover approximately 3 kb. These two genes are separated by a junction sequence containing a splicing acceptor site.

The AEV genome is hence completely devoid of the pol gene and partially devoid of the env and gag genes. As a result, the replication of the virus requires simultaneous infection by a helper virus. In this work, the helper virus is RAV-2, the genome of which is shown in FIG. 3.

By genetic recombination "in vitro", it has been possible to create deletions, respectively, in the v-erbA and v-erbB genes. From the analysis of the transforming power of the mutant viruses thereby created, it emerges that:

the v-erbB gene on its own provides for the transformation of fibroblasts "in vitro" and the induction of sarcomas "in vivo";

the v-erbA gene alone appears to be incapable of inducing any transformation "in vitro" and the results of the "in vivo" analyses relating to the v-erbA gene remain ambiguous;

the deletion of the v-erbA gene alone causes a reduction in the transforming power on erythrocyte precursors "in vitro".

This oncogenic power of AEV, mainly localised on erbB, can be used as a means for controlling the transformation of cells exposed to this virus. From this standpoint, the transforming nature of retroviruses in general, and AEV in particular, is to be compared with that which results from the genes coding for the expression of dominant markers (xgprt gene or Neor gene) which are employed in the second embodiment of the invention. The advantage of this oncogenic transformation induced by a retrovirus is that it brings about physiological changes which endow the transformed cells with increased power of multiplication. In particular, the special capacity of transformed fibroblasts to grow in soft agar offers a method for selecting the cells which have incorporated and are expressing the viral genome.

With the object of preserving the function of the v-erbB gene which is essential to the development of the oncogenic power, the foreign genes are inserted either in the v-erbA gene or downstream of the v-erbB gene and before the right LTR sequence.

The choice of these insertion sites must take into account, in addition to the preservation of the v-erbB gene, that of other "sensitive" regions of the virus (initiation and stopping of transcription, polyA addition site in the LTR, splicing signals).

The experiments carried out showed that the foreign gene could be oriented in either direction relative to the reading direction of the viral genome.

Insertion of the foreign gene in the EcoRI(2) site of AEV led to two active vectors, AEVdelta(28) and AEVdelta(17), incorporating the gene for human delta-globin, which vectors can be used by replacing the globin gene by another gene.

In the experiments carried out, the elements for expression of the foreign gene were not studied systematically, but it is clear that the foreign gene can be preceded by expression elements which will be peculiar to it, independently of the expression elements already present in the virus.

For reasons of convenience, the constructions were carried out first on plasmids which contain a composite DNA sequence corresponding to the reverse transcript of a virus as described above.

Naturally, this plasmid can contain a portion of bacterial plasmid with, for example, an origin of replication in prokaryotes and, for example, a character of resistance to an antibiotic, as is known, but a phage or cosmid can also be employed.

Cultured chick fibroblasts transfected with the recombinant viruses in the form of DNA clones gave rise to the production of infectious viral particles with very high titers.

Analyses of the DNA in the proviruses and the RNA derived from the viral particles showed that the recombinant viruses retain and transmit the DNA fragment of the human delta-globin gene.

Choice of human delta-globin gene

By way of example of a foreign gene, the genes for globin were used, especially for human delta-globin, since it is clear that it may be readily demonstrated after its incorporation in the genome of chick cells. The particular choice of the delta-globin gene rests on various criteria:

the mapping and sequence have been established, and a deltaPst clone (FIG. 7) exists;

the size of the deltaPst fragment does not exceed 2.3 kb, and a fragment of much larger size would lead to an increase in the size of the viral genome, which might inhibit its encapsidation in the viral particles;

this sequence finally has a restriction map which facilitates its insertion in the AEV genome.

Non-oncogenic vectors

In this second type of vector, the v-erbB gene is no longer expressed, preferably because it has been at least partially deleted. Thus, in the vectors-which will be studied in detail, the 1.6 kb of nucleotide sequences originating from the erbB gene are removed and replaced by the Neo$^r$ structural gene of the prokaryotic transposon Tn5. This results in three DNA recombinants, pXJ1, pXJ2 and pXJ3.

Naturally, the use of the Neo$^r$ structural gene is only described by way of example, and it is naturally possible to use other genes for resistance as a marker gene.

The pXJ1 clone contains a single copy of the Neor gene oriented in the same transcriptional direction as that of AEV. The heterologous sequences introduced are 1.2 kb long. They are composed of the sequence originating from a phage mp11 cloning polylinker, nucleotides derived from a BglII Linker, a BglII-HincII fragment of the bacterial transposon Tn5 in which the gene Neo$^r$ is situated, and a short sequence of the HSV tk gene carrying, in particular, the addition site for polyA sequences.

In the clone pXJ3, two copies of the Neo$^r$ gene are introduced at the site of the deleted erbB gene. These two identical genes are arranged in tandem in the same transcriptional orientation as that of the deleted erbB gene. In this recombinant, the heterologous sequences introduced are 2.4 kb long. The junctions between the heterologous sequences and the retroviral vector are the same as in the case of pXJ1.

In short, the only difference between wild-type AEV and the retroviral vectors constructed is that the verbB viral oncogene is replaced by the prokaryotic Neo$^r$ gene.

When bacteria are transformed by the vectors carrying the Neo$^r$ gene (pXJ1, pXJ2 and pXJ3), they acquire resistance to kanamycin.

When the concentration of kanamycin exceeds 50 µg/ml of culture, the bacterial cells transformed by pXJ1 and pXJ3 show 10 times greater growth than that of cells transformed by pXJ2.

The clone pXJ5 devoid of Neo$^r$ genes does not induce any resistance to kanamycin in the transformed bacteria.

Thus, it is possible that the AEV LTR contains sequences which perform the role of prokaryotic promoter However, the possibility cannot be ruled out that the Neo$^r$ gene is activated by potential promoters present in the retained pBR322 sequences.

These vectors were introduced into mouse L cells and quail QT6 cells by transfection. Only the vectors pXJ1 and pXJ3 induce in the transfected cells resistance to doses of G418 greater than 300 µg/ml. These results demonstrate that transcription of the Neo$^r$ gene is initiated at the promoter carried by the left LTR.

The vector carrying the two Neo$^r$ genes in tandem induces resistance in the transfected cells with a much lower frequency than the vector pXJ1. This property might originate either from the greater size of the vector pXJ3, which would reduce its capacity for integration in the cell genome, or from the existence of recombinations between the two repeat Neo$^r$ sequences, leading to more or less extensive deletions of these sequences. The interaction between the termination of the translation of the first gene and the initiation of that of the second might also exert an effect on the expression of these two genes.

It is clear that, apart from its use by way of a marker, the Neo$^r$ gene must be considered as an example of the expression of a foreign gene in a vector according to the invention. Nevertheless, in this type of vector, the Neo$^r$ gene will be used as a marker and another foreign gene will be incorporated in the vector.

Other non-oncogenic vectors originate from AEV in which the two v-erbA and v-erbB oncogenes are inactivated by partial or complete deletion.

In this case, it is possible to insert two foreign genes which may be expressed simultaneously, especially if one of these genes is situated between the splicing sequences and if the other gene is situated outside the splicing regions and downstream of the latter. One of these two genes will then be translated from the genomic RNA, and the other from the subgenomic RNA.

The experiments demonstrated the fact that it was possible to vary the amount of genomic RNA relative to the amount of subgenomic RNA.

Thus, insertion of the Neo$^r$ gene was accomplished first in a sequence in which several initiation codons were allowed to persist in different reading phases, and then in a construction containing only initiation codons in a same reading phase. This latter construction proves to affect the genomic RNA/subgenomic RNA production ratio in a direction favourable to the production of genomic RNA, that is to say to the expression of the gene carried by the site positioned at 5'. The use of this vector has led to the development of a specific titration method for avian viruses carrying the Neo gene.

The vectors which are especially useful according to the invention are those in which a single restriction site has been inserted between the two splicing acceptor and donor sites and a single restriction site downstream of these splicing sites; under these conditions, it is possible to insert in these sites foreign genes which will correspond to a genomic RNA and a subgenomic RNA during transcription.

These sites will preferably be positioned so that the inserted genes can be in phase in the reading frame, and it is said that the genes are synchronised.

These genes will preferably be positioned to be under the dependence of the 5' LTR promoter.

One of the genes in question may, for example, be a selection gene such as Neo$^r$, or the like.

As is seen from the above description, the foreign genes inserted in the vectors according to the invention were frequently expressed as a result of expression elements present in the virus genome, but it is naturally possible to insert upstream of the foreign gene specific expression elements which provide for increased expression of the foreign protein; these expression elements may, for example, be virus promoters, especially avian virus promoters.

Naturally, when the vector is a plasmid, cosmid or phage, it will also contain the elements necessary for the replication of these latter in prokaryotic cells, as well as the elements characteristic of this type of vector, such as the cos ends in the cosmid.

The present invention relates, in addition, to the cells transfected by the vectors according to the invention, whether these vectors are in the form of viruses or plasmids. It is clear that primary transfection will generally be accomplished with vectors of the plasmid type, that is to say the AEV will be in the form of the DNA of its genome; but in the presence of the DNA of the helper virus, transfected avian cells will in this case be transformed and release recombinant viruses which will be able to infect other cells.

This process enables a very high cell transformation yield to be obtained, which will be especially valuable in cell cultures "in vitro". This type of process also enables stocks of vector viruses to be formed, which may be used subsequently in the place of plasmid vectors.

In the case where the cells are transfected by oncogenic vectors, their selection is natural without it being necessary to add a selection agent, while in contrast, in the second type of non-oncogenic vector, which contains a gene coding for resistance to an antibiotic, culturing will have to be performed in the presence of the said antibiotic.

The cells in question can be of various types, but are preferably avian cells, especially hematopoietic cells, germ cells or cells of the fibroblast type.

The preferred cells for employing the vectors of the invention are chick embryo fibroblasts.

Finally, the invention relates to the process for preparing a specified protein, in which process there are cultured cells modified by an AEV vector according to the invention in which the foreign gene codes for the said protein, and in which process the protein is recovered from the cell culture. It should be noted that the cells in which the virus has been integrated in the form of provirus can constitute cell lines, and the cells can, moreover, be either avian or non-avian cells.

When the infection is performed at the level of the germ cells, especially at the level of the egg, transformed animals can be obtained.

The examples below will enable other characteristics and advantages of the present invention to be demonstrated these examples are described with reference to the diagrams, wherein.

Figure 1:
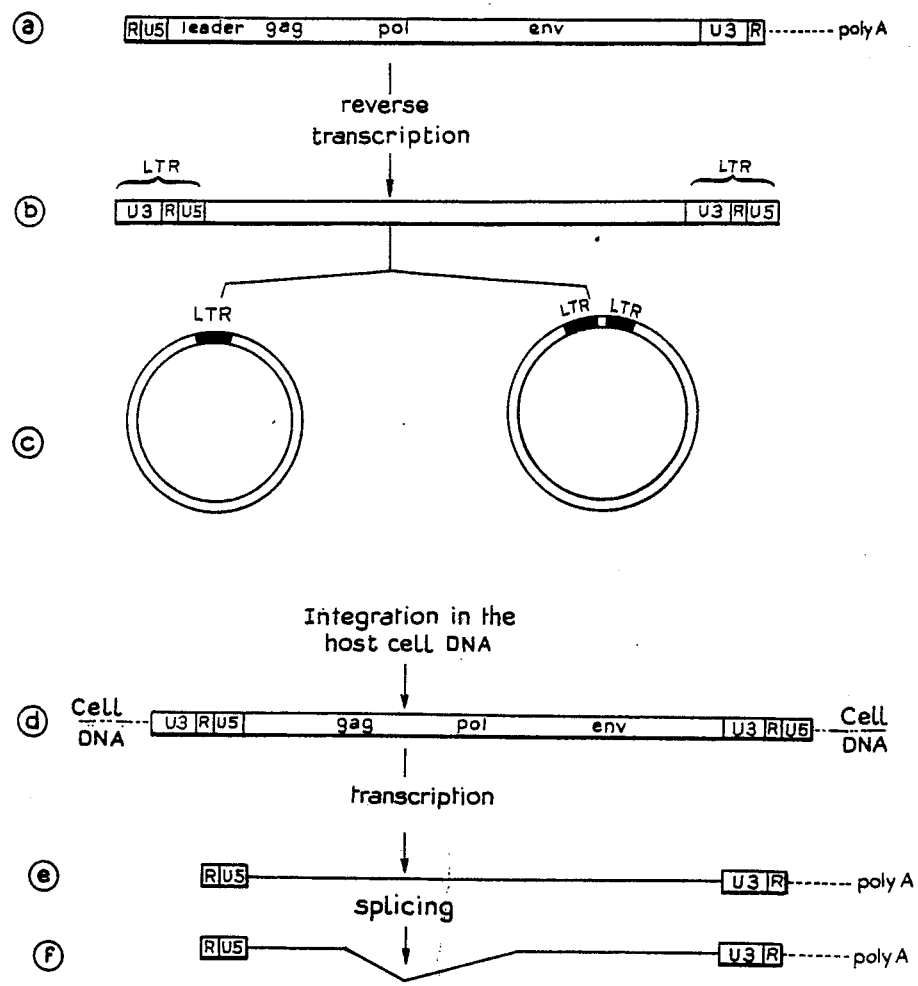
FIG. 1 is a scheme of various stages of development of a retrovirus.
Figure 2:
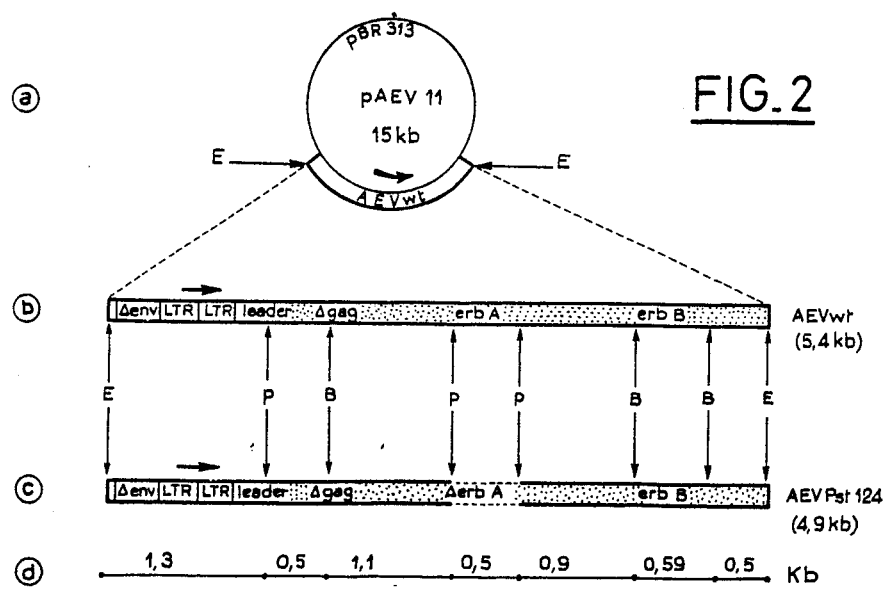
FIG. 2 shows the structure of the AEVwt and AEVPst124 genome.
Figure 3:
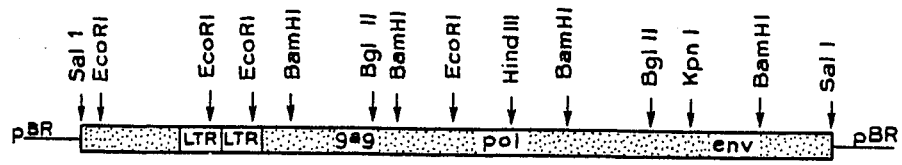
Figure 4:
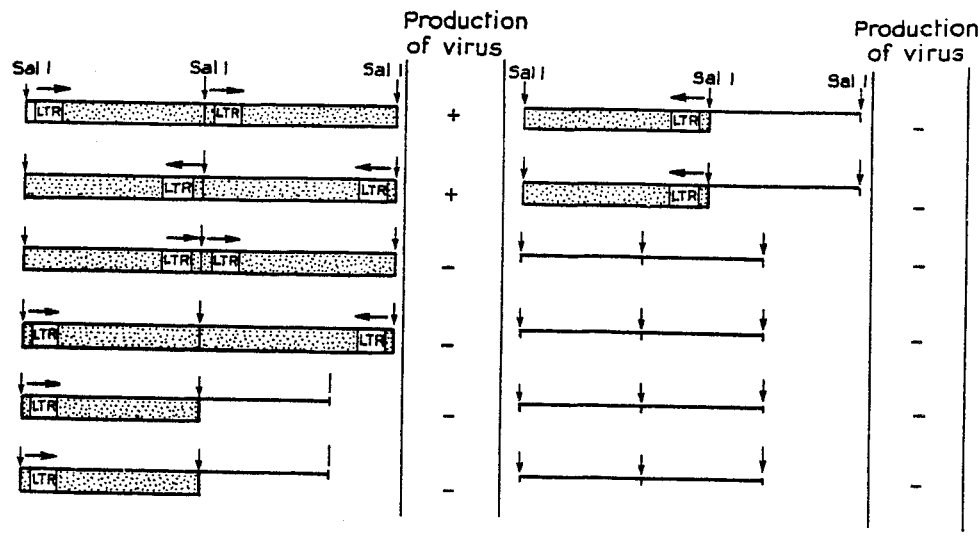

FIG. 3 shows the genome of the RAV2 helper virus in the form of double-stranded DNA, FIG. 4 shows the "in vitro" formation of DNA viral genomes carrying an LTR at each end; the DNA of the pRAV2 clone is opened by SalI and then subjected to the action of the ligase under conditions which promote the formation of concatemers between the molecules; in the mixture thus produced, a few molecules are surrounded by an LTR at each end; they may be integrated in the DNA of the host cell genome and give rise to virions, although only the arrangements as dimers are shown here;

■:3 RAV2 viral sequence

Figure 5:
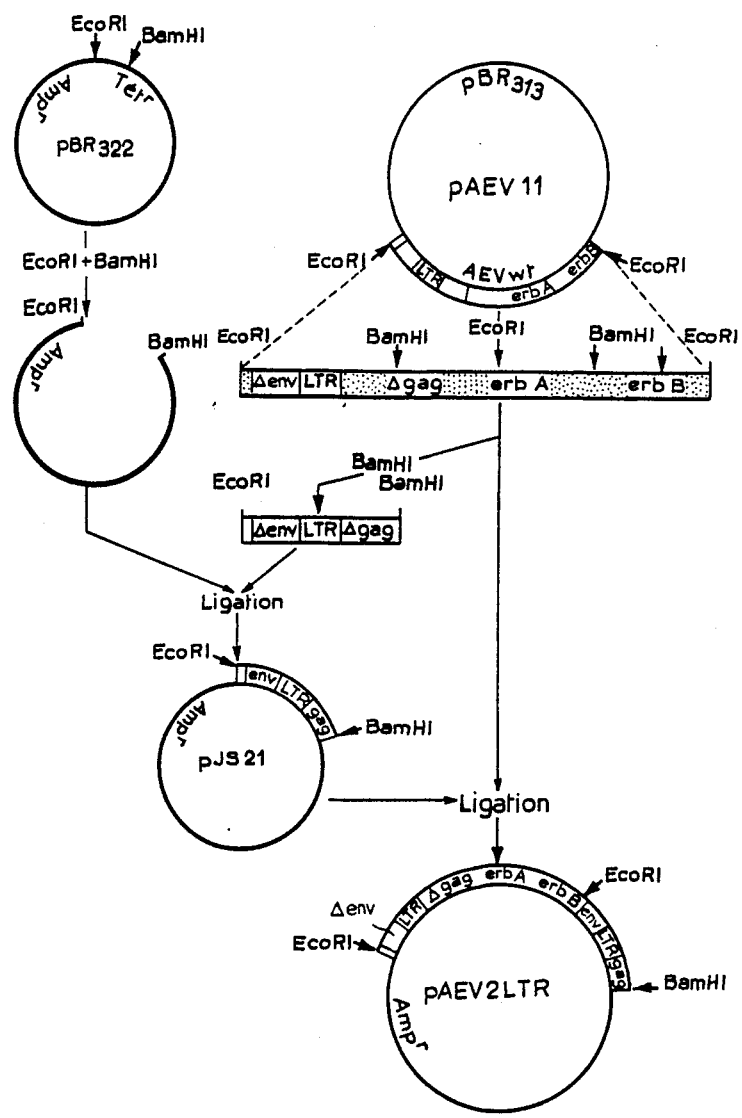
Figure 6:
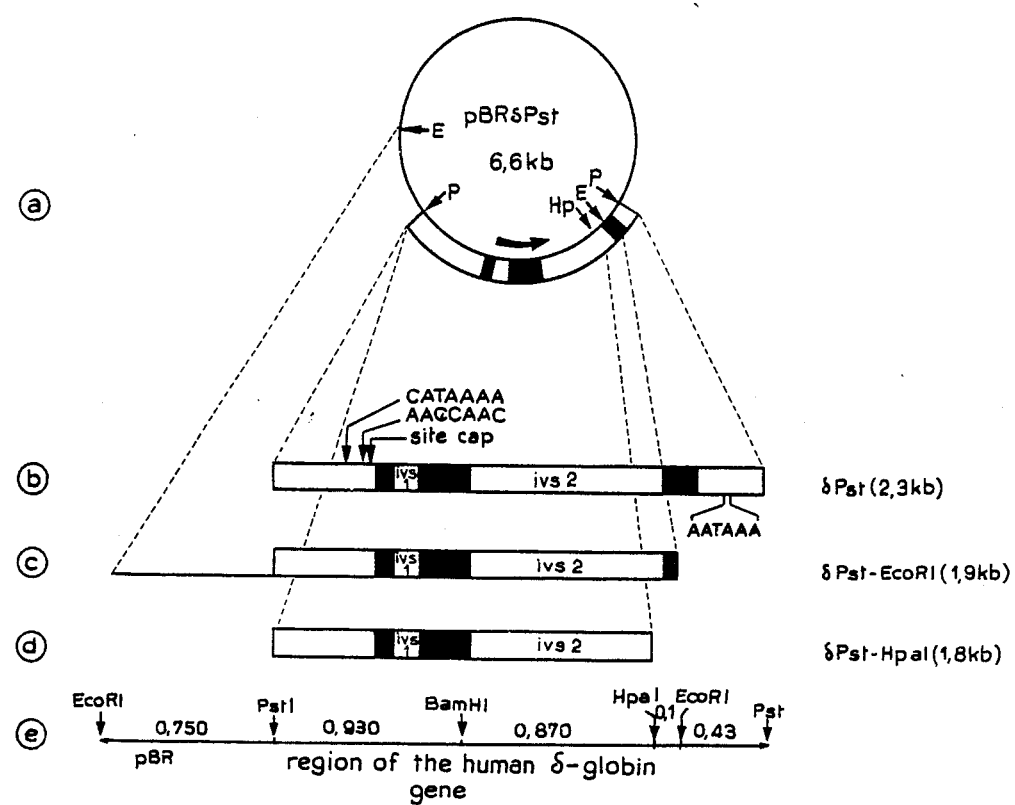
Figure 7:
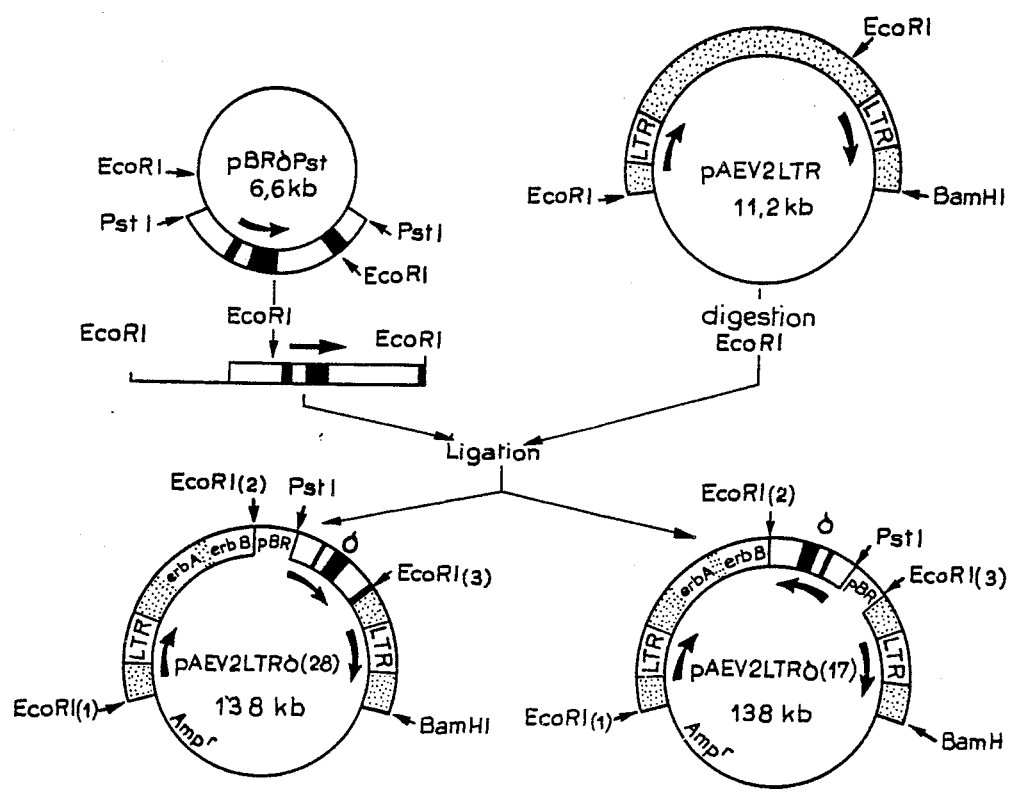
Figure 8:
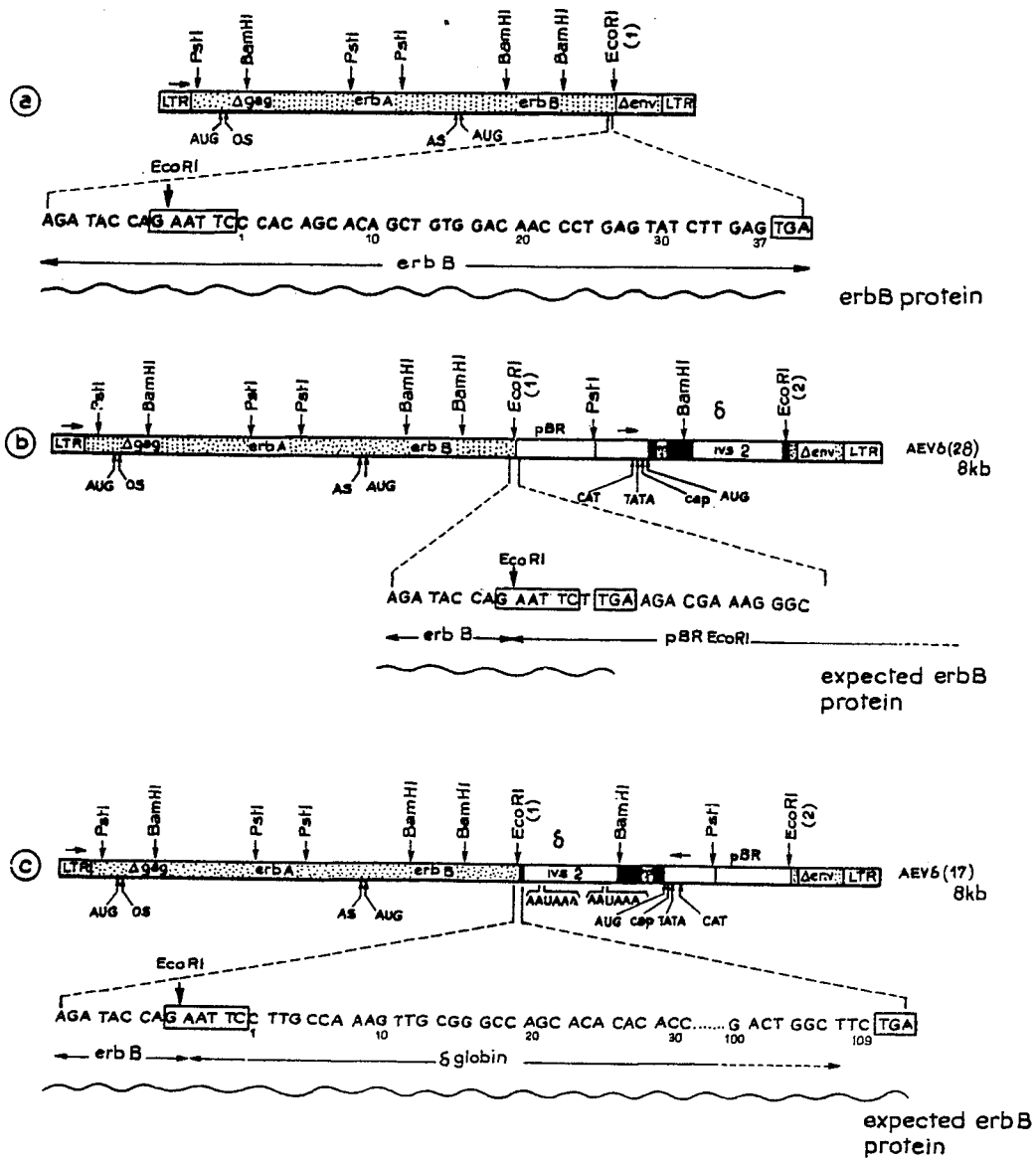
Figure 9:
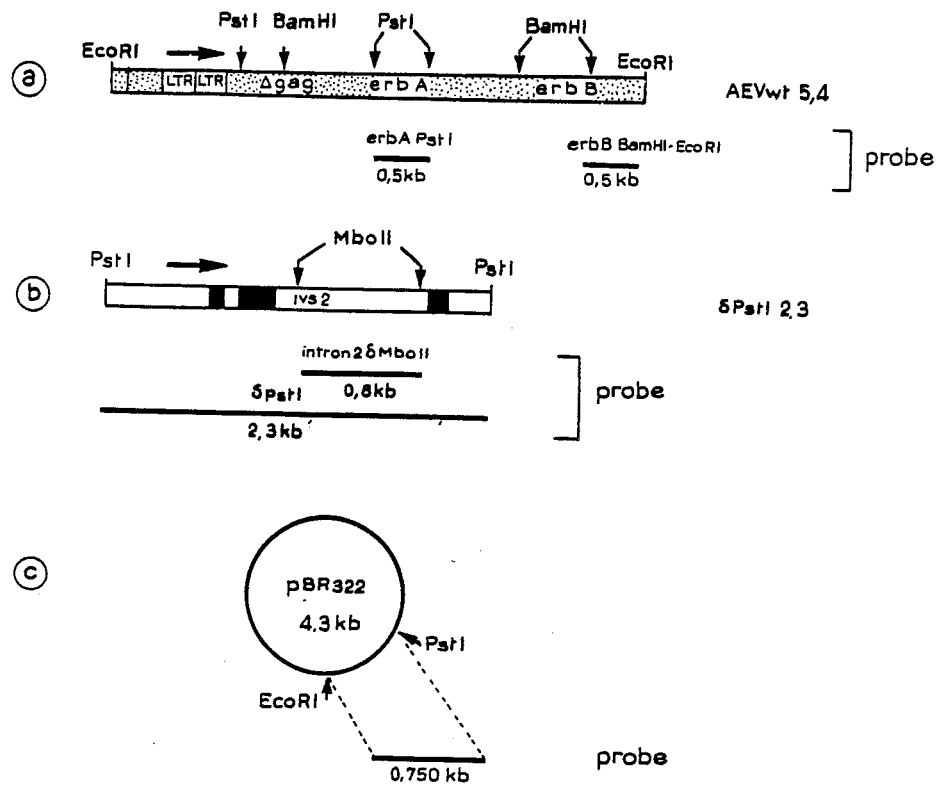
Figure 10:
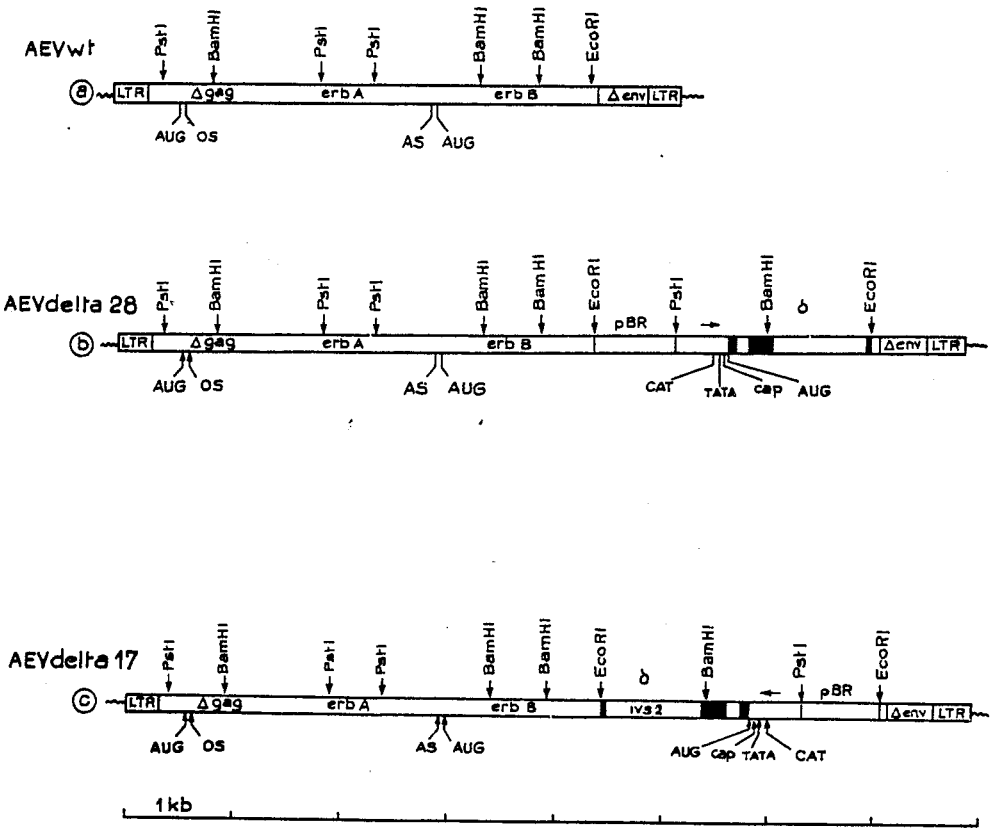
Figure 11:
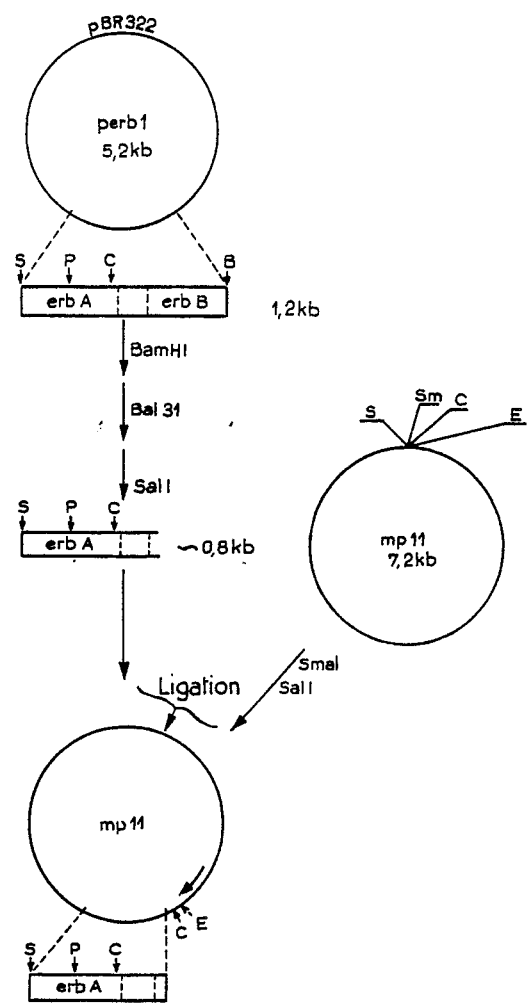
Figure 12:
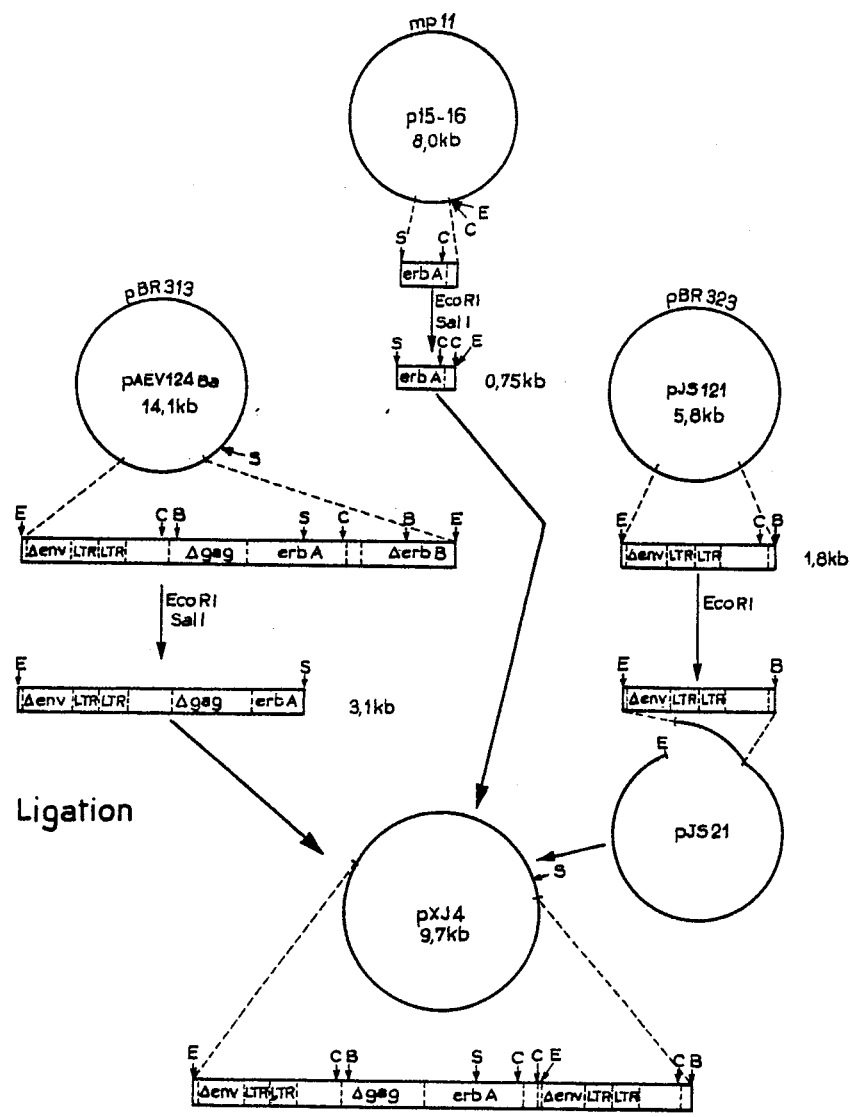
Figure 13:
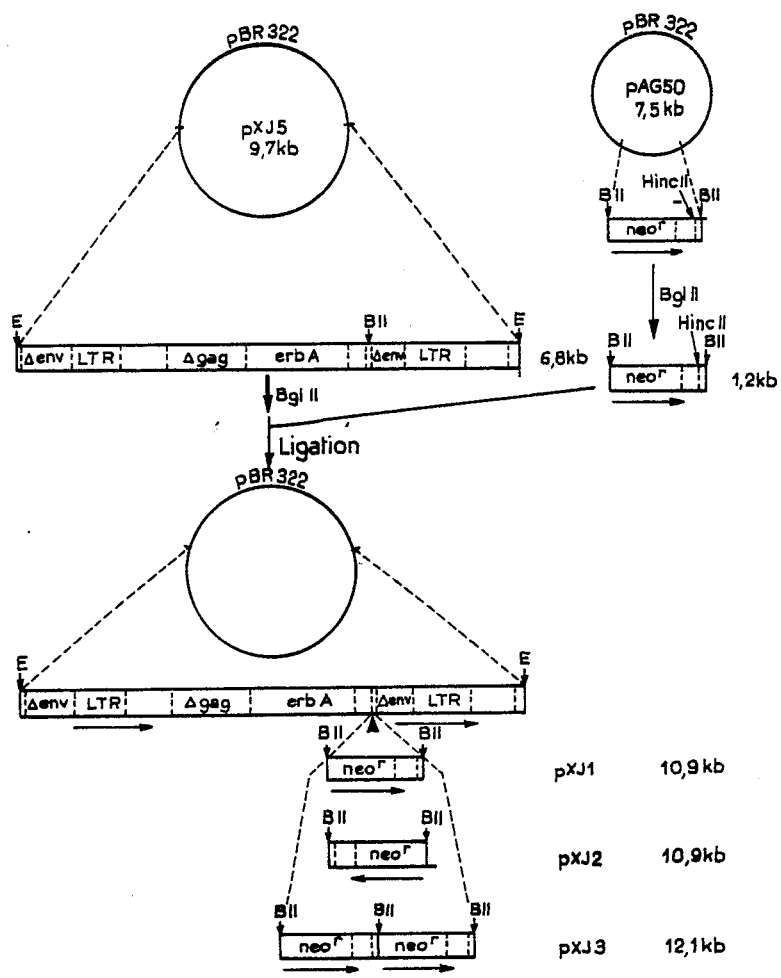
Figure 14:
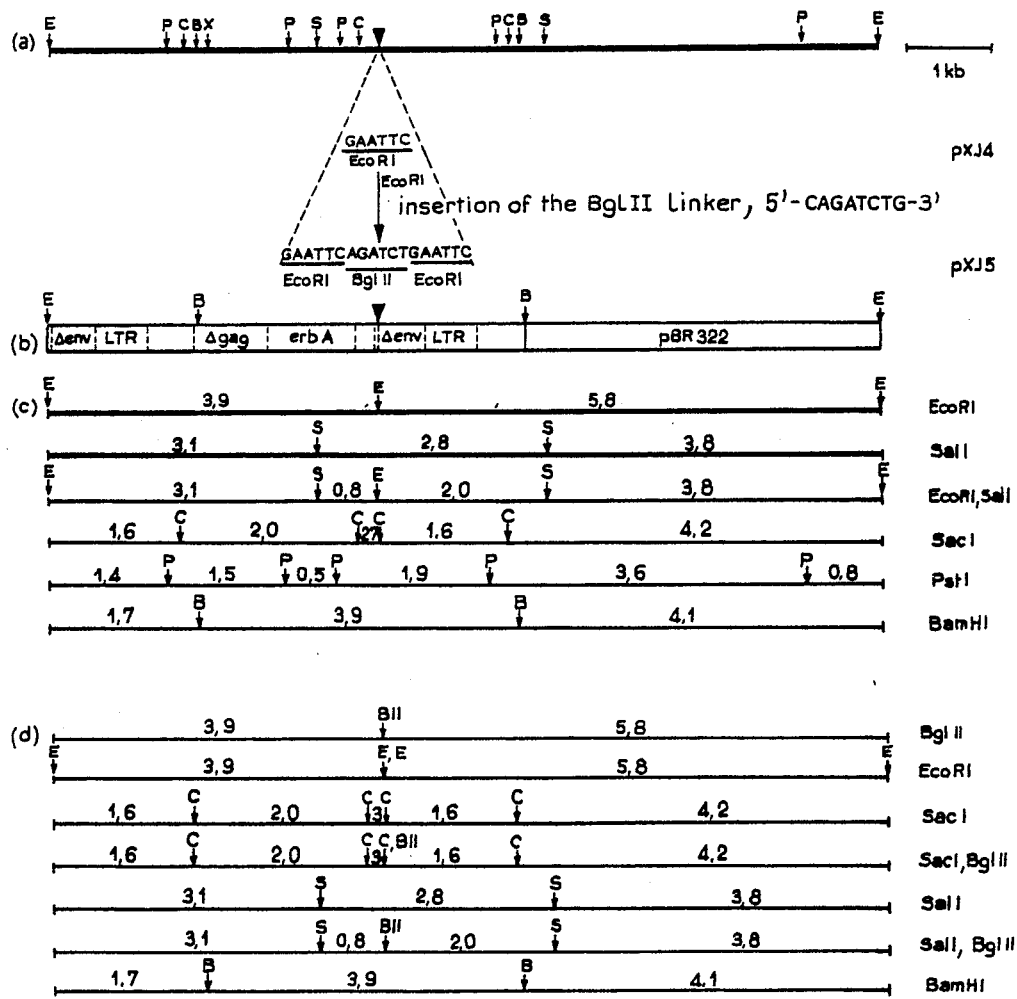
Figure 19:
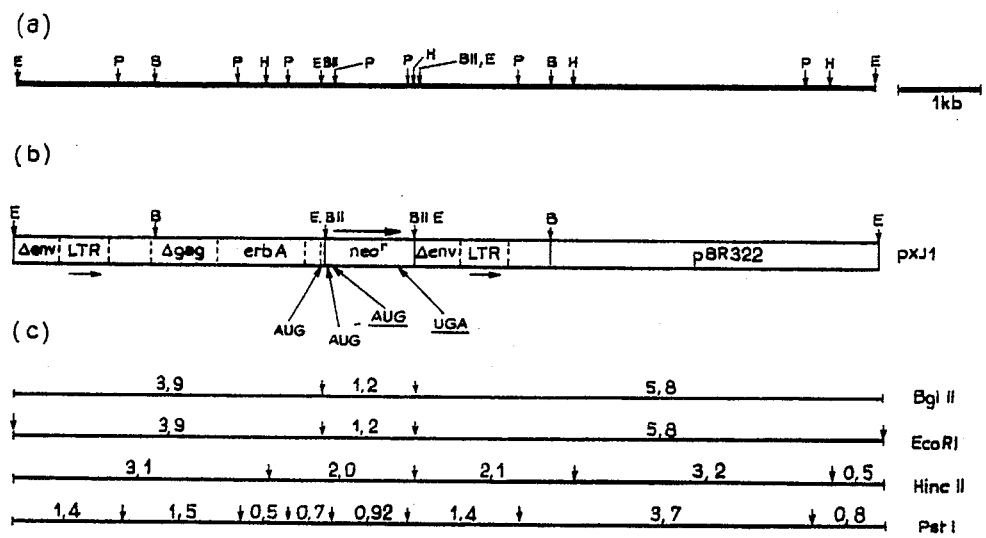
Figure 20:
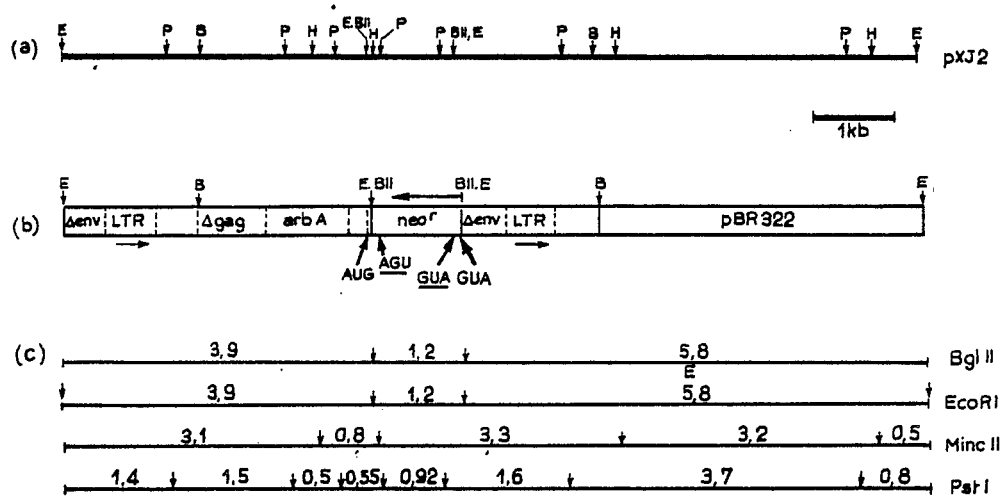
Figure 21:
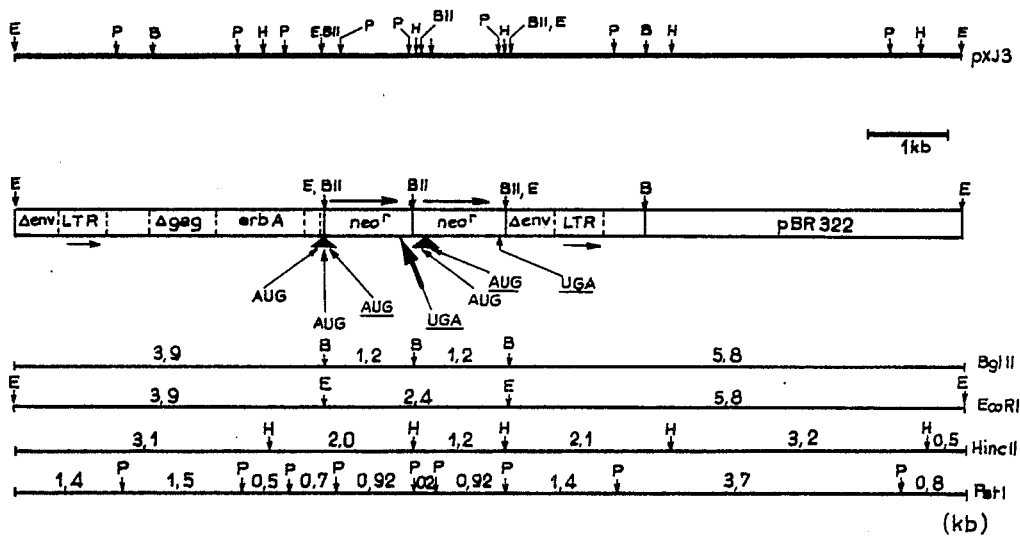

—:3 plasmid pBR322 sequence the direction of the arrows indicates the transcription direction, FIG. 5 shows the construction of an AEV DNA genome containing LTR sequences at each end (pAEV2LTR), FIG. 6 shows the map of the recombinant plasmid pBRdeltaPst and various fragments of the human deltaglobin gene used in the experiments on construction of transfer vectors, FIG. 7 shows the construction of recombinant vectors of the pAEV2LTRdelta type, FIG. 8 shows the structure of AEVdelta(28), FIG. 9 shows cloned DNA fragments used as probes, FIG. 10 shows theoretical restriction maps of the proviral genomes of the wild type (a), mutant AEVdelta(28) (b), and mutant AEVdelta(17) (c), FIG. 11 shows the cloning of Bal31 fragments in mp11, FIG. 12 shows the construction of the AEV mutant pAEVΔerbB(pXJ4), FIG. 13 shows the introduction of the Neo$^r$ gene of the Tn5 transposon into the retroviral vector pXJ5, FIG. 14 shows the structures of the clones pAEV-ΔerbB (pXJ4,pXJ5) and the construction of pXJ5, FIG. 15 shows the structure of the AEV genome cloned in pBr313, FIG. 16 shows the cloning of the HincII-BamHI fragment (1.2 kb) containing the junction between v-erbA and v-erbB in bacteriophages mp8 and mp11 in the form of double-stranded DNA, FIG. 17 is a comparison of the nucleotide sequences between the v-erbB gene of AEV and that of AEV-H (YAMAMOTO et al., 1983), ---: identical nucleotides, the different nucleotides are indicated in the AEV sequence, the BamHI site in the 5' region of v-erbB is underlined, FIG. 18 shows the nucleotide sequence of selected Bal31 fragments, the non-coding sequence interposed between the erbA gene and the erbB gene is numbered; the limits of the v-erbA gene and v-erbB gene sequences and that of the cloning vector mp11 are indicated by vertical lines; the horizontal lines show v-erbB gene sequences retained after digestion with Ba131; the restriction sites in the mp11 sequences are underlined;
p15-16, p-15-21, p15-25, p15-28 names of clones, CAG: presumed splicing acceptor site;

FIG. 19 shows the structure of the pXJ1 clone and the map of the restriction sites;

FIG. 20 shows the map of the the restriction sites and the structure of pXJ2;

FIG. 21 shows the map of the restriction sites and the structure of pXJ3;

FIG. 22 shows the junction sequences between the Neo$^r$ gene and the retroviral vectors in the clones pXJ1 and pXJ3.

Figure 23:
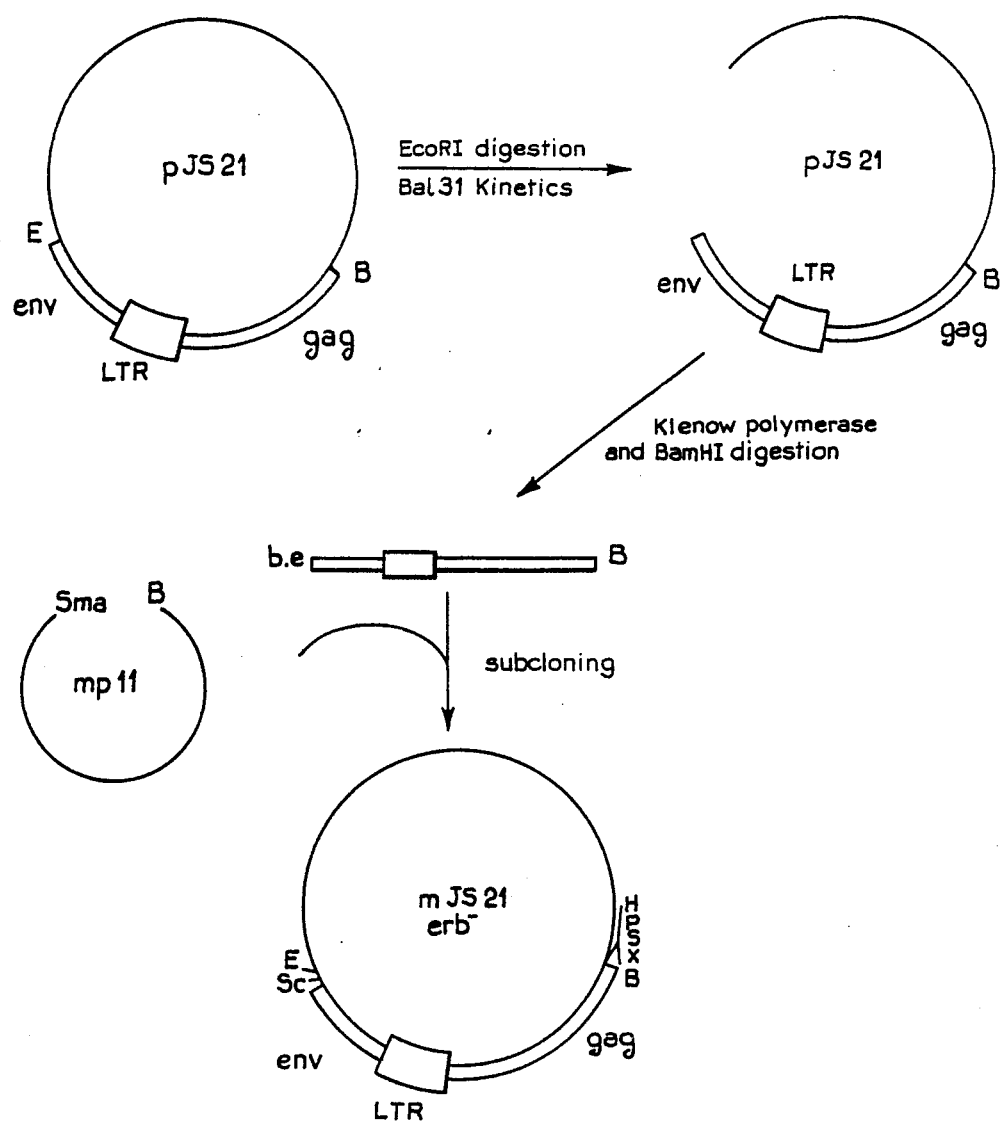
Figure 24:
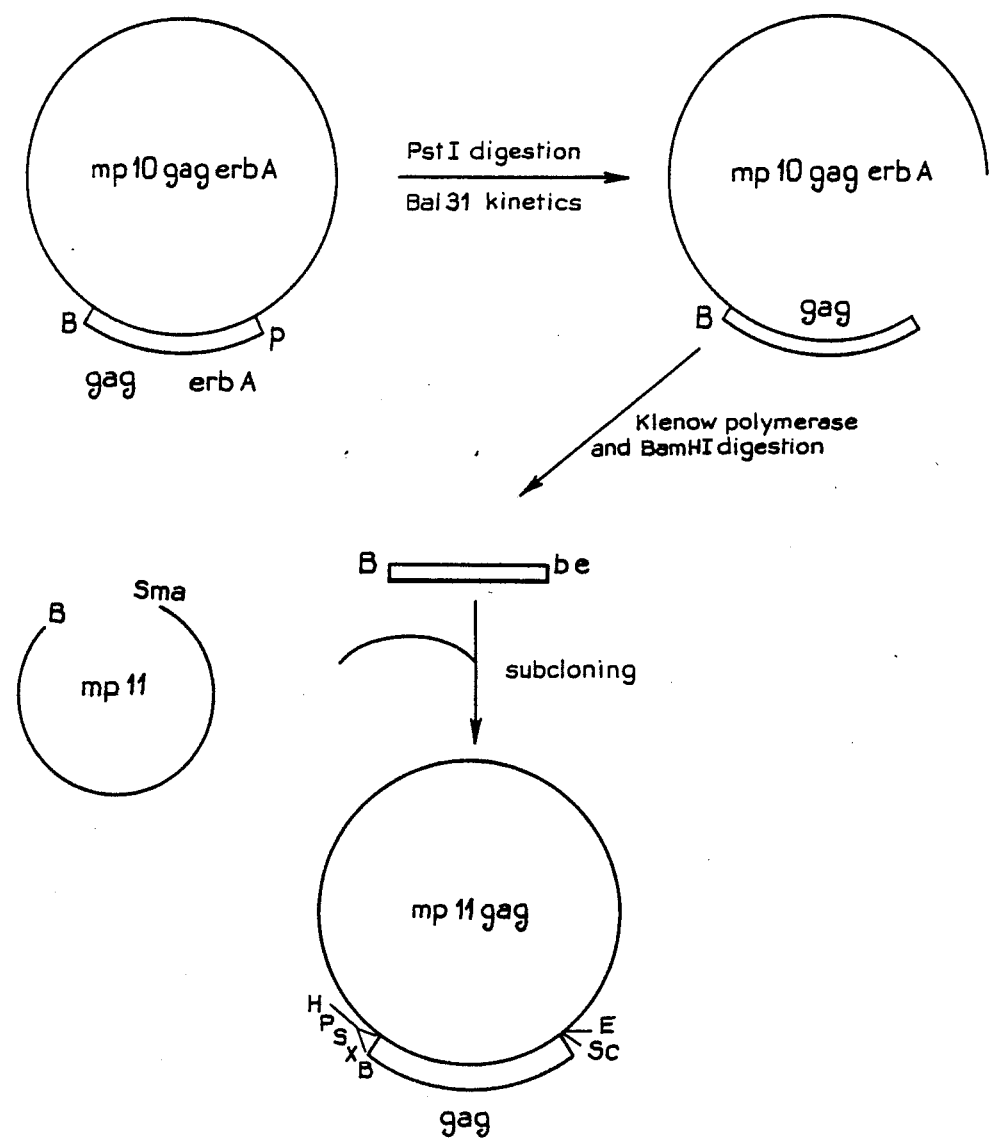
Figure 25:
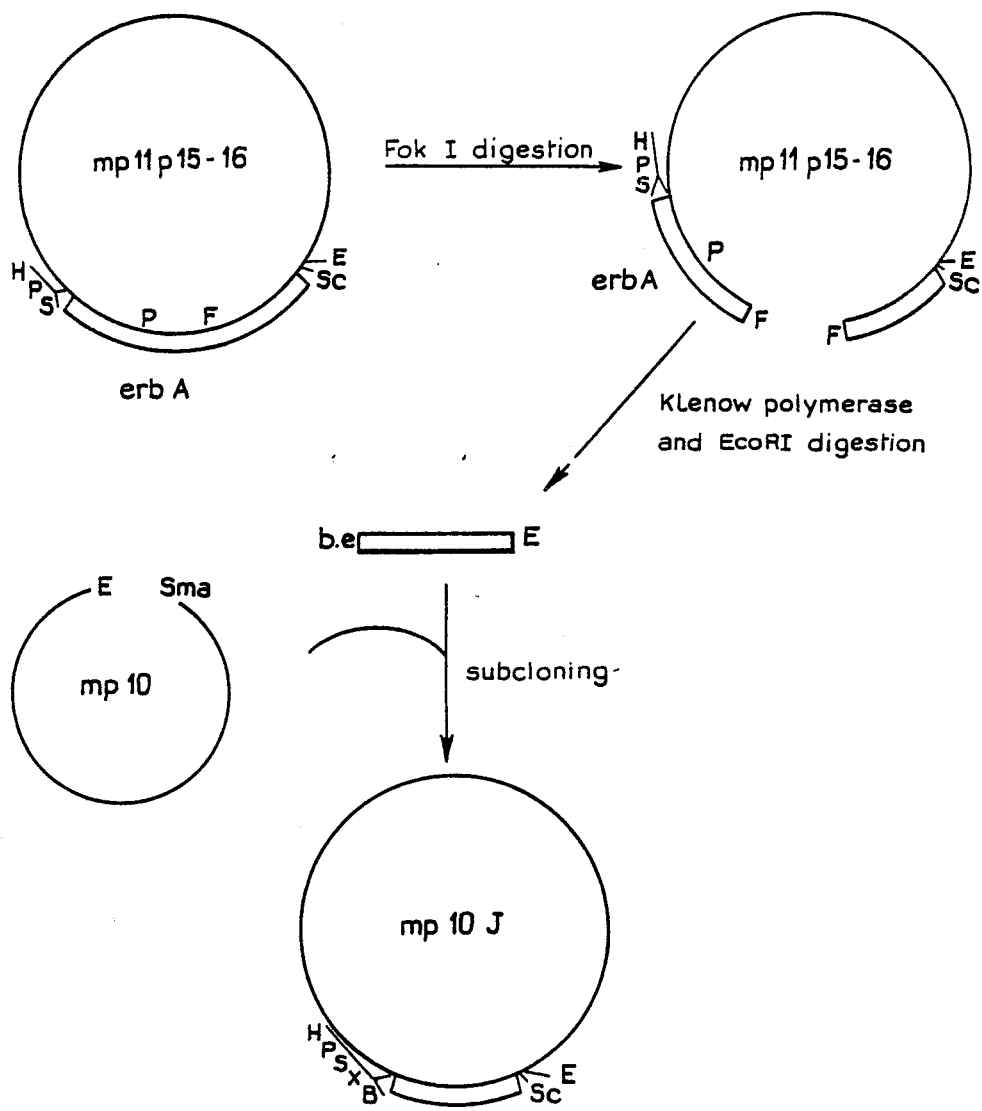
Figure 26:
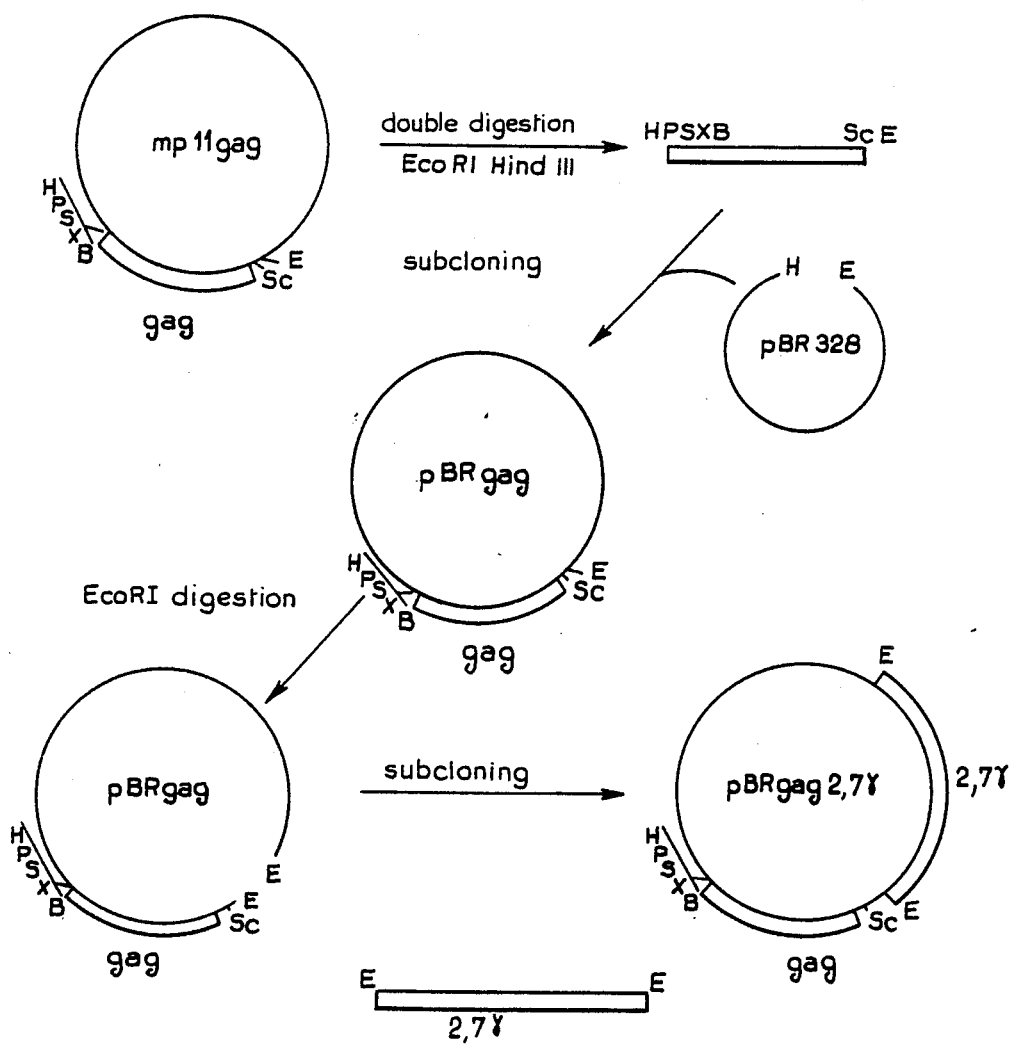
Figure 27:
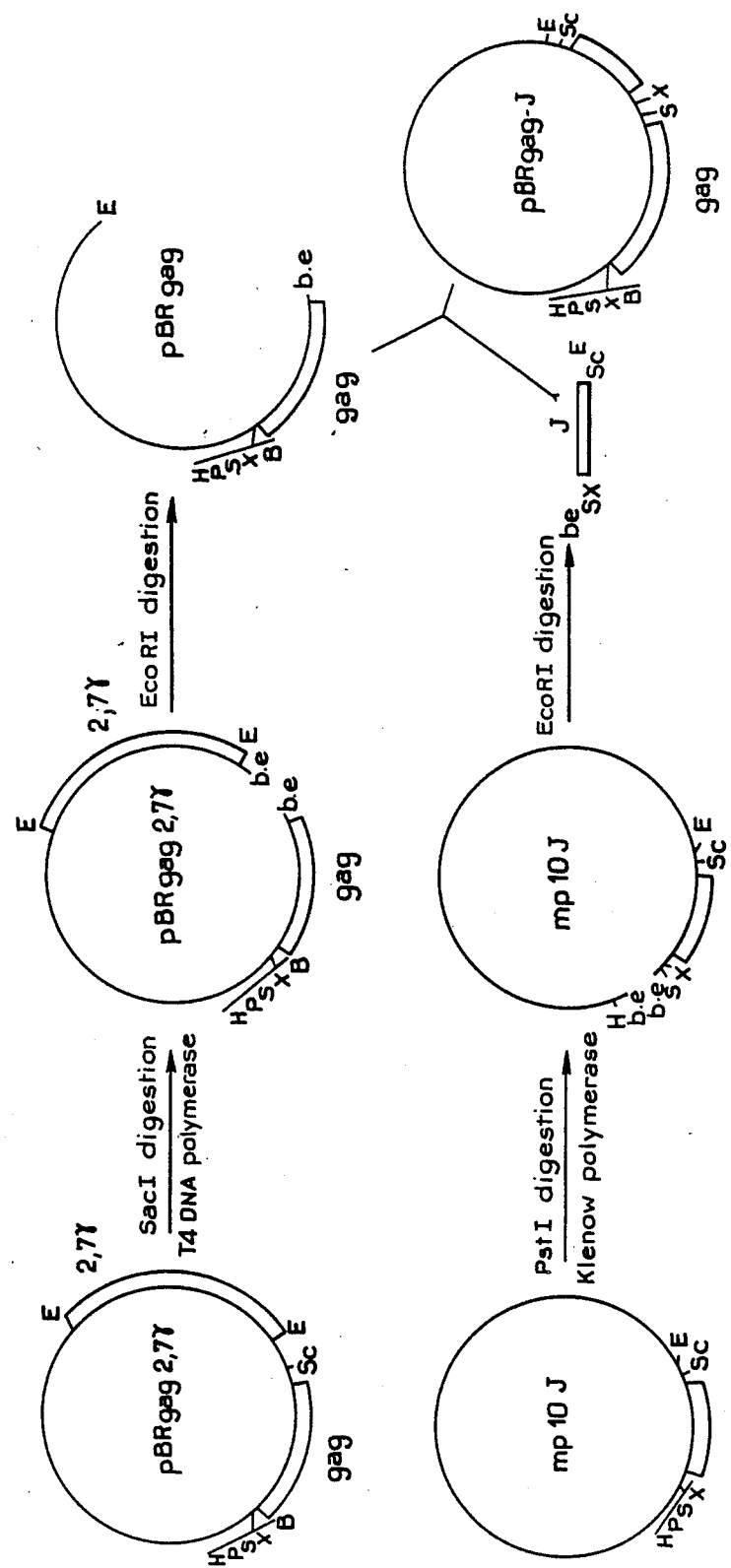
Figure 28:
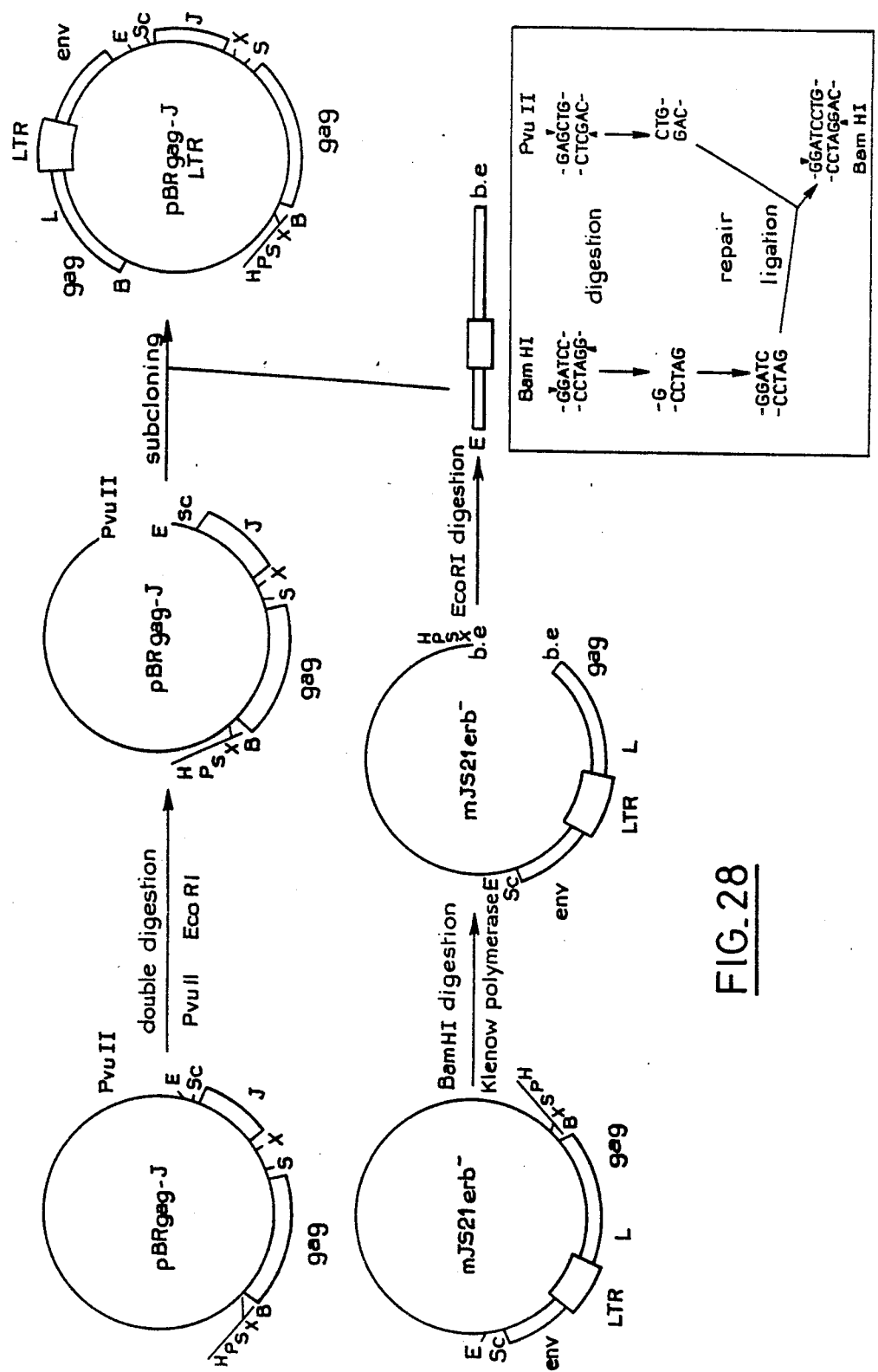
Figure 29:
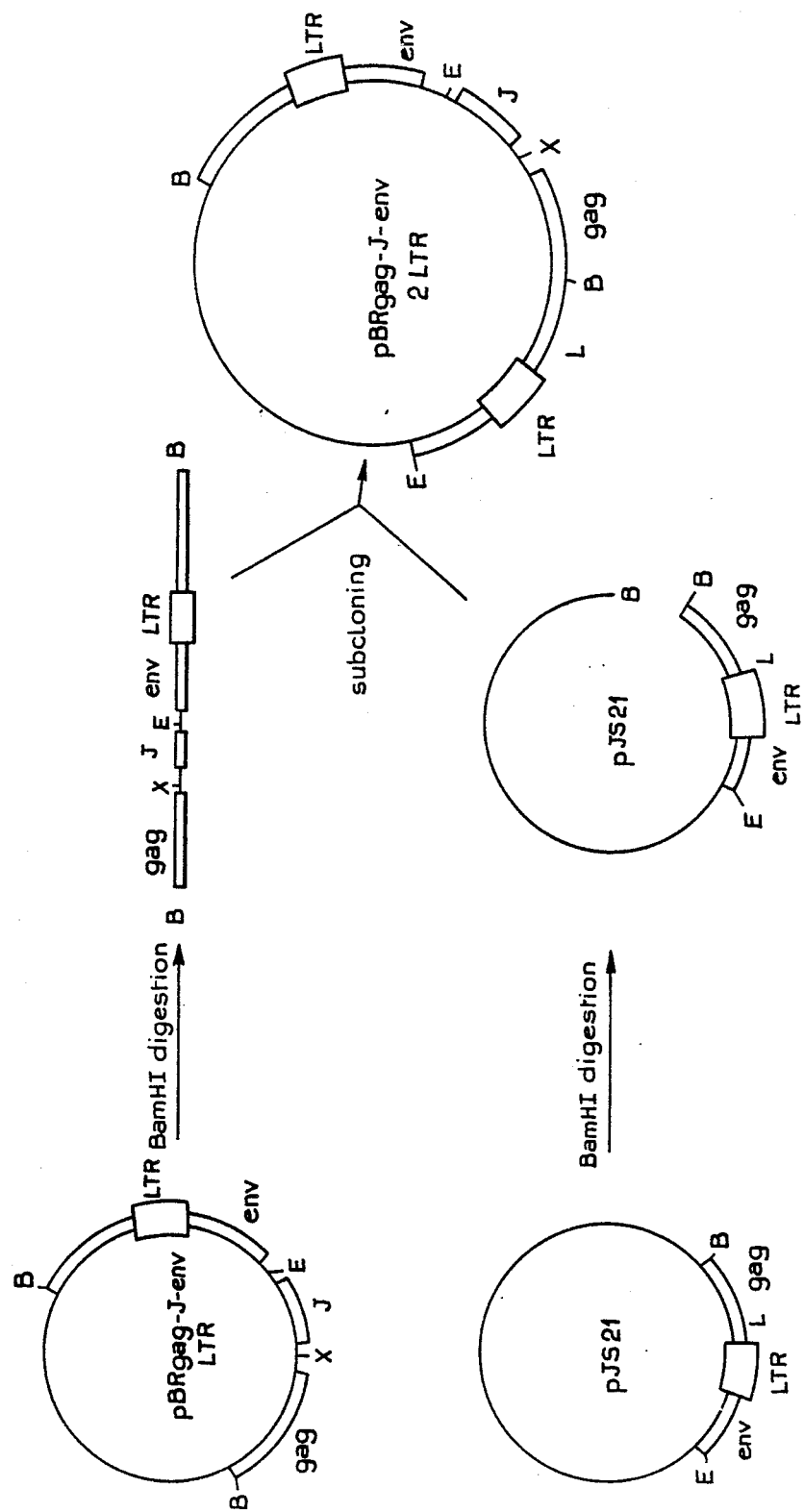
Figure 30:
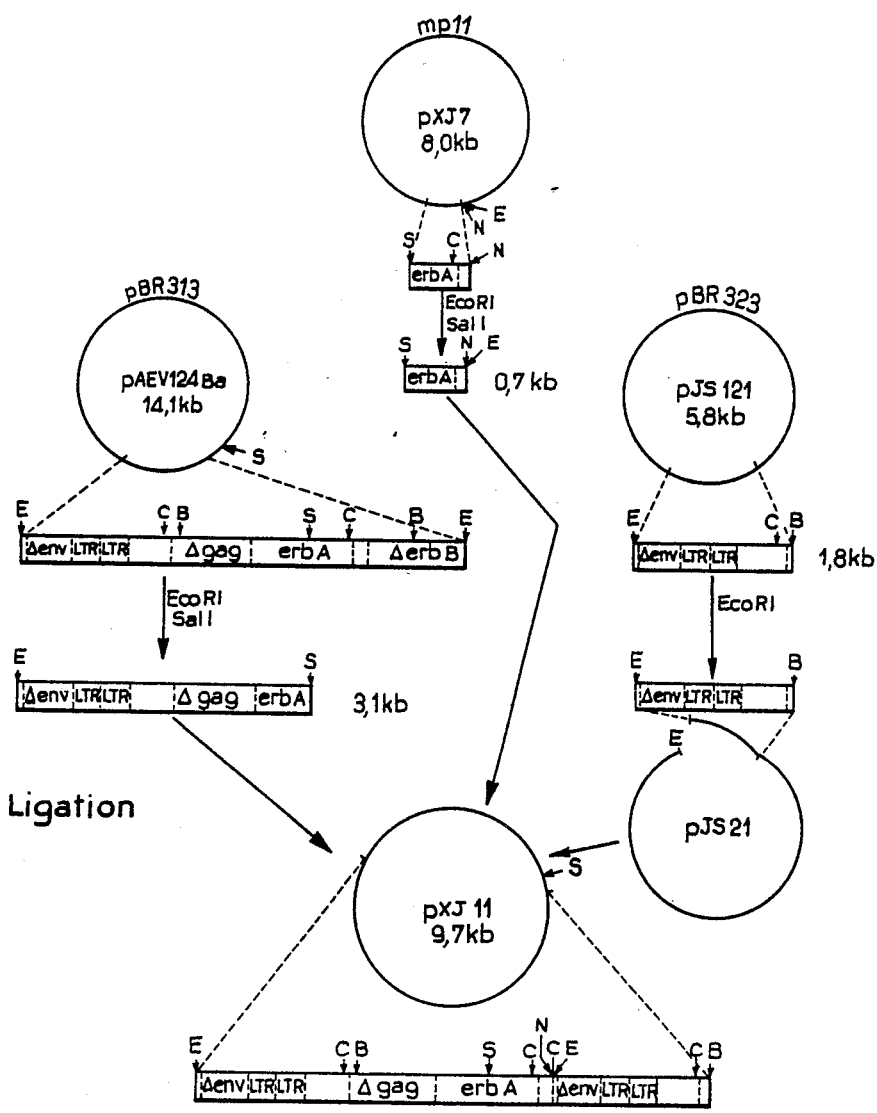
Figure 31:
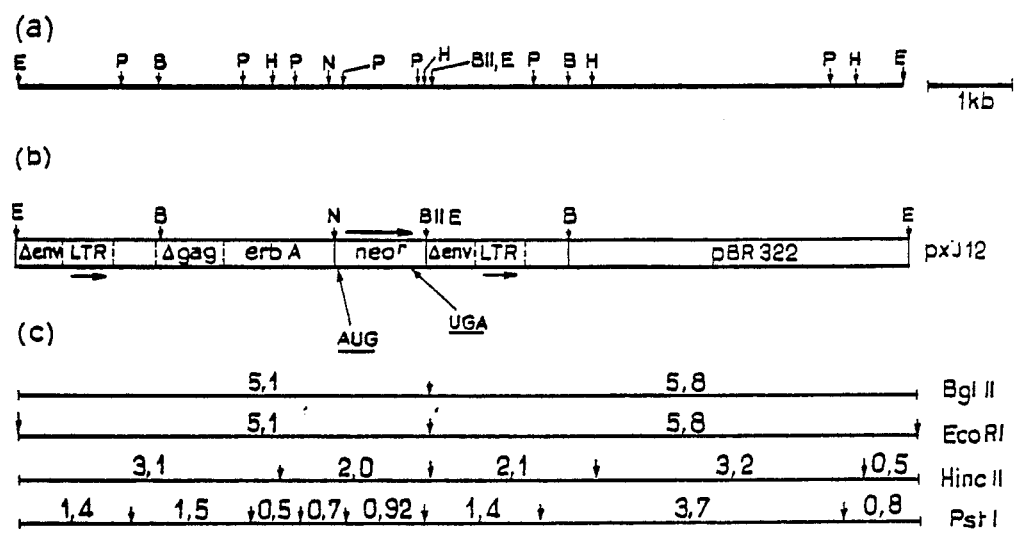

FIG. 23 shows the preparation of the clone mJS21 erb$^-$;

FIG. 24 shows the preparation of the clone mp11-gag;

FIG. 25 shows the preparation of the clone mp10-J;

FIG. 26 shows the preparation of the clone pBRgag-2,7 γ;

FIG. 27 shows the preparation of the clone pBRgag-J;

FIG. 28 shows the preparation of the clone pBRgag-J-env LTR;

FIG. 29 shows the preparation of the clone pBRgag-J-env 2LTR;

FIG. 30 shows the preparation of the clone pXJ11;

FIG. 31 shows schematically the structure of pXJ12.

These figures and the corresponding nucleotide sequences form an explicit part of the present description, but have not been repeated in order to avoid encumbering the said description.

The restriction sites are abbreviated in the following manner:

| | | |
|---|---|---|
| B | BamHI | |
| BII | BglII | |
| E | EcoRI | |
| F | FokI | |
| P | PstI | |
| C | SacI | |
| Sm | SmaI | |
| S | SalI | |
| X | Xho | } FIGS. 1 to 22 |
| H | HincII | |
| X | XbaI | } FIGS. 23 to 31 |
| H | HindIII | |

I—GENERAL TECHNIQUES (A) Culturing of Eukayotic Cells (1) L cells (mouse) are maintained in culture at 37° C. and with 5% of $CO_2$. The cells are subcultured regularly every 3 or 4 days. The culture medium is composed of DMEM (Gibco) supplemented with 10% of foetal calf serum, 2 mM glutamine, 2.2 mg/ml of sodium bicarbonate, 100μg/ml of streptomycin and 100 iu/ml of penicillin.

(2) The chick fibroblasts are obtained after subculturing primary cultures prepared from 10- to 11-day embryos maintained in culture in HAM F10 medium (Gibco) supplemented with 10% of tryptose phosphate broth (Gibco), 2 μg/ml of Polybrene, 5% of calf serum, 1% of inactivated chicken serum, 2 mg/ml of sodium bicarbonate, 100 μg/ml of streptomycin, 100 iu/ml of penicillin and 60 mg/ml of Fungizone.

(B) Preparation of Nucleic Acids (1) Preparation of DNA (a) Preparation of plasmids The bacterial strains E. coli HB101 or C600RS harbouring the plasmids used are cultivated on L. broth medium (bactotryptone 10 g/l, yeast extracts 5 g/l, NaCl 5 g/l) supplemented with 5 ml/l of 20% strength glucose solution and with the appropriate antibiotics.

The plasmids are isolated by the clarified lysate technique according to EL-GEWELY and HELLING (1980), and purified on a caesium chloride gradient. The purified plasmid DNA is resuspended in double-distilled water and stored at +4° C.

(b) Preparation of chick fibroblast DNA

The chick fibroblast DNA is obtained after homogenisation of the cells in 100 mM Tris-HCl pH 7.4, 10 mM EDTA$Na^2$, 100 mM NaCl and 0.5% SDS. Pronase is added at 0.5 mg/ml and the mixture is incubated at 37° C. for 8 to 12 hours. The DNA is extracted with phenol/chloroform and chloroform/isoamyl alcohol. The solution is adjusted to 200 mM NaCl and precipitated once with isopropanol and then twice with ethanol. The pellet resuspended in T-E buffer (10 mM Tris pH 7.4, 1 mM EDTA) is treated with RNase (50 μg/ml) for 1 hour at 37° C., and then pronase (100 μg/ml) for 1 hour at 37° C.

The DNA solution is extracted once with phenol and twice with chloroform/isoamyl alcohol, and the DNA is finally precipitated with 2 volumes of ethanol. The DNA pellet thus purified is resuspended in T-E buffer and stored at +4° C.

(2) Digestion with restriction enzymes

The restriction enzymes are supplied by Boehringer and are used under the incubation conditions given by the manufacturer. In general, 1 to 4 units of enzyme are used to digest 1 μg of DNA for 2 hours at 37° C. The enzyme reaction is stopped by incubation at 65° C. for 5 to 10 minutes.

(3) Preparation of RNA

The glassware used for the extraction of the RNA is sterilised beforehand by heating in a Pasteur steriliser for at least 2 hours. The tubes used for the extraction are further treated with 0.1% strength diethyl pyrocarbonate (Sigma). The buffers are sterilised at 120° C. for 30 to 40 minutes.

(a) Total cellular RNA

The total cellular RNA is extracted from eukaryotic cells according to the technique of AUFFRAY and ROUGEON (1980), starting with $20 \times 10^6$ to $50 \times 10^6$ chick fibroblasts infected with retroviruses.

After centrifugation of the cells at 800 rpm, the cell pellets are frozen in liquid nitrogen for 10 to 15 minutes and resuspended in a denaturing buffer [3M LiCl, 6M urea, 0.01M sodium acetate pH 5, 0.01M vanadyl-/ribonucleic complex (BRL)]. The solution is adjusted to 0.01% SDS and stored overnight at +4° C. The RNA is recovered after centrifugation at 10,000 rpm for 20 minutes at 4° C. The pellet is washed with an 8M urea, 4M LiCl solution, and then resuspended in double-distilled water. The RNA solution is extracted once with phenol and once with phenol/chloroform, and the RNA is finally precipitated with 2 volumes of ethanol in the presence of 0.2M sodium acetate pH 5.

(b) Preparation of poly(A)+RNA

Poly(A)+RNA is prepared according to the technique described by LONGACRE and RUTTER (1977), by column filtration.

200 to 500 μg of total RNA are placed on a column containing 200 to 300 mg of type 3 oligo(dT)-cellulose (Collaborative Research). Filtration of RNA is performed in a buffer containing 10 mM Tris pH 7.4 and 500 mM KCl. The eluate is recycled twice on the column. The poly(A)+RNA is released by the elution buffer (10 mM Tris pH 7.4). The poly(A)+RNA solutions are adjusted to 200 mM sodium acetate pH 5 and the poly(A)+RNA is precipitated with two volumes of ethanol. The pellets are resuspended in double-distilled water and stored at −20° C.

(c) Preparation of virions RNA

The virions are recovered in the culture supernatants of chick fibroblasts infected with the virus. In practice, when the cultures infected with the virus contain a majority of transformed cells, the culture medium is changed for fresh medium. The virions are then collected 24 hours later. The supernatants are then centrifuged once at 2,000 rpm for 10 minutes to remove the cell debris. The virions are then sedimented by ultracentrifugation in a 50.2 Ti rotor at 16,000–18,000 rpm for 2 hours at 4° C. The pellets containing the virions are resuspended in 10 mM Tris pH 7.4 containing 10 mM EDTA, 100 mM NaCl and 10 mM vanadyl/ribonucleic complex. 0.1% SDS and proteinase K (0.5 mg/ml) are added and the suspension is incubated for 1 hour at 37° C., and then extracted twice with chloroform, and the RNA is precipitated with two volumes of ethanol.

(C) Electrophoresis and Transfer of Nucleic Acids to Nitrocellulose Filter (1) Electrophoresis and transfer of DNA 15 to 20 μg of total DNA previously digested with restriction enzymes are placed on a horizontal 1% agarose gel. Electrophoresis is performed in E-T buffer (40 mM Tris pH 7.5, 20 mM sodium acetate, 2 mM EDTA) containing 0.5 μg of ethidium bromide for 12 to 16 hours. The gel is denatured by immersion in a 0.5 N NaOH, 1.5M NaCl solution for 2 to 3 hours and then neutralised with 500 mM Tris-HCl pH 5.6, 300 mM NaCl for 3 hours at room temperature. The transfer of the DNA is performed by applying a nitrocellulose membrane (Sartorius or Schleicher and Schüll )u on the agarose gel overnight, according to the technique of SOUTHERN (1975).

(2) Electrophoresis and transfer of RNA 15 to 20 μg of total RNA or poly(A)+ RNA or 2 to 5 μg of poly(A)+ RNA are denatured with formaldehyde according to LEHRACH et al. (1977). The RNA is equilibrated with MOPS buffer (20 mM morpholinopropanesulphonic acid pH 7, 5 mM sodium acetate, 1 mM EDTA) and denatured in the presence of 6% of formaldehyde and 50% of formamide at 65° C. for 5 to 10 minutes, and then cooled rapidly in ice. Fractionation of the denatured RNA is performed on a horizontal 1% to 1.5% agarose gel containing 6% of formaldehyde, in MOPS buffer. Migration takes place for 16 to 20 hours at 30–40 volts and at room temperature, with recycling of the buffer. The transfer of the RNA from the gel to a nitrocellulose filter is carried out according to the technique of SOUTHERN (1975) modified by THOMAS (1980). The nitrocellulose filter, rinsed with double-distilled water, is equilibrated for 5 to 10 minutes in 20×SSC before being applied on the gel. The transfer lasts overnight at 4° C. The filter is then recovered and dried under a lamp for 5 to 10 minutes.

(D) Preparation of Radioactive Probes 0.4 μg to 0.5 μg of various DNA fragments used as probes are labelled "in vitro" by nick translation (RIGBY et al. 1977). The reaction takes place in a final volume of 100 μml containing 50 mM Tris-HCl pH 7.8, 5 mM $MgCl_2$, BSA 500 μg/ml, 10 mM beta-mercaptoethanol, 3.5 μM dGTP, 3.5 μM dATP, 40 μCi of (alpha-$^{32}$P)dCTP and 40 μCi of (alpha-$^{32}$P)TTP (specific activity 400 Ci/mmol-Amersham), 2 pg of DNaseI (Worthington) and 4 to 5 units of DNA polymerase (Boehringer). The mixture is incubated for 2 hours at 15° C. The reaction is stopped by adding 50 μl of 250 mM EDTA and the labelled DNA is separated from the non-incorporated nucleotides on a column of Sephadex G-50 or Biogel (Bio-Rad A, 1.5 m).

(E) Hybridisation of the Filters

After transfer of either DNA or RNA, the filters are dried at 70° to 80° C. for 2 hours, and treated with a prehybridisation buffer (50 mM Tris-HCl pH 7, 3 X SSC, $RNA_t$ 20 μg/ml, salmon sperm DNA 20 μg/ml, 1×Denhardt's solution, 50% formamide) for 8 to 20 hours at 42° C. Hybridisation is carried out in the same buffer containing 5–10×$10^6$ cpm of the radioactive probe for 24 48 hours at 42° C.

When hybridisation is complete, the filters are washed once in 2 X SSC for 1 hour at 42° C. and then twice in 0.1 X SSC, 0.1% SDS for 45 minutes at 50° C., and are finally rinsed 4 times in 0.1 X SSC for 5 minutes. After being dried, the filters are exposed for autoradiography on film (Kodak Royal X Omat AR) at −80° C. with reinforcing screens. The exposure lasts from 5 hours to several days.

(F) Dehybridisation of the Filters

The filters hybridised a first time with a $^{32}$P-labelled probe are dehybridised in SSC at 70°–75° C. for 10 to 15 minutes. They are dried and exposed for 48 hours in autoradiography. The filters are treated with the prehybridisation buffer and used with a fresh probe.

II—TECHNIQUES USED FOR "IN VITRO"GENETIC RECOMBINATION (A) Isolation of Cloned Fragments in Plasmids (1) Isolation after agarose gel electrophoresis 50 μg to 100 μg of plasmid DNA containing the fragment to be isolated are digested with the restriction enzymes which enable the fragment to be released. The DNA fragments are then separated by electrophoresis on horizontal agarose gel overnight at 30–40 volts. The region of the gel containing the fragment to be isolated is then cut out. The DNA is extracted from the agarose by one or other of the following two techniques:

(a) Electroelution technique

The cut-out region of the gel containing the fragment to be isolated is placed in a dialysis bag containing E-T buffer (40 mM Tris pH 7.5, 20 mM sodium acetate, 2 mM EDTA). The bag is subjected to an electric field (30–40 volts) in a jar containing E-T buffer. The elution of the DNA is followed by brief illumination with ultraviolet light. When elution is complete, DNA is extracted 3 to 4 times with isoamyl alcohol and when precipitated with two volumes of ethanol.

(b) So-called "freeze-squeeze" technique (TAUTZ and RENZ, 1983)

The piece of gel containing the fragment to be isolated is equilibrated in 10 times its volume of a solution containing 300 mM sodium acetate pH 7 and 1 mM EDTA, with stirring for 30 to 45 minutes and shielded from the light. The piece of gel is placed in a 0.6- ml Eppendorf tube pierced at the bottom and stoppered with glass wool, and the assembly is frozen in liquid nitrogen. The tube containing the piece of gel is placed in a 1.5-ml Eppendorf tube and then centrifuged at 12,000 rpm for 10 minutes at room temperature. The recovered solution containing the fragment to be isolated is adjusted with a solution containing 1 mM $MgCl_2$ and 10% acetic acid, and then precipitated with 2.5 volumes of ethanol. The pellet is rinsed successively with a mixture containing 70% ethanol. The pellet is briefly dried and then resuspended in T-E buffer.

(2) Sucrose gradient

50 μg to 100 μg of plasmid DNA previously digested with restriction enzymes are placed on a 5–20% sucrose gradient. The gradient is centrifuged for 14 to 16 hours at between 30,000 and 36,000 rpm in an SW 41 rotor at 20° C. The bands located under ultraviolet light are recovered with the aid of a pipette.

The DNA is dialysed in T-E buffer overnight, then purified with phenol and chloroform and finally precipitated with ethanol.

(B) Dephosphorylation of the 3' Ends of the DNA

The DNA is incubated in the presence of bacterial alkaline phosphatase or BAP (BRL) for 1 hour at 65° C. In general, 10 units of BAP are used per mole of DNA 3' end to be dephosphorylated. The enzyme is then removed by two successive extractions with phenol/chloroform, and the DNA is recovered by precipitation with ethanol.

(C) Ligation

The ligation of DNA fragments is performed in a buffer composed of 600 mM Tris pH 7.6, 66 mM $MgCl_2$, 100 mM DTT, and 4 mM ATP in the presence of phage T4 ligase (Boehringer) at a concentration of 2 u/μg of DNA. The DNA molecules to be ligated are added in equimolar amounts at a final concentration of 5–10 μg/ml. The final mixture, which does not exceed 60 μl, is incubated overnight at 65° C.

(D) Addition of Linkers

PstI linkers were used for construction of the pAEV-deltaΔHpa recombinants. In this particular case, the linkers are added to the HpaI site of the human delta-globin gene.

0.5 μg of PstI linkers (BRL) are phosphorylated in a mixture containing 60 mM Tris-HCl pH 7.8, 10 mM $MgCl_2$, 15 mM beta-mercaptoethanol, 4 units of a polynucleotide kinase (Boehringer), 50 μM ATP and 10 HCi of (gamma-$^{32}$P)ATP. The reaction is incubated at 37° C. for 30 minutes. The mixture of phosphorylated PstI linkers is added to 5 μg of plasmid pBRdeltaPst opened beforehand at the HpaI site and dephosphorylated. The mixture is subjected to the action of T4 ligase overnight at 15° C.

(E) Identification of Bacteria

The recombinant plasmid DNA is introduced into C-600 RS bacteria made competent according to the technique of MANIATIS et al. (1982). The transformed bacteria are then plated on an agar dish containing the appropriate antibiotics.

(F) Identification of the Plasmids in the Bacterial Clones

(1) Transfer of bacterial colonies to a filter

This technique is applied in the case where the recombinant plasmids sought represent a small proportion among the possible different recombinant plasmids. It permits rapid screening over a large number of bacterial colonies. A filter paper (Whatman) sterilised by heating at 150° C. for 2 hours is applied for 10 to 15 seconds on the agar dish containing highly individualised bacterial colonies. After transfer, the filters are dried in the air for 5 to 10 minutes and then treated in 0.5M NaOH for 5 minutes and placed in an incubator at 37° C. for 1 hour. The filters are then treated for 5 minutes twice in each of the following three baths, with agitation: 0.5M NaOH–0.5M Tris pH 8–2×SSC; and they are finally rinsed in ethanol and dried in air.

The colonies containing the recombinants sought are identified by hybridisation of the filter with a DNA probe labelled with (alpha-$^{32}$P)dCTP by nick translation.

The filters are prehybridised in a mixture of 50% formamide and 5 ×SSC for 2 hours at 37°–42° C. Hybridisation is performed in the same mixture in the presence of suitable specific probes for 24 to 48 hours at 42° C., The filters are washed, respectively, for 30 minutes in 50% formamide and 5 ×SSC at 37°–42° C., and for 30 minutes 4 times in 2 ×SSC at room temperature. The filters are finally rinsed in ethanol then dried in air and exposed for autoradiography for 2 to 4 hours. The colonies containing the DNA fragments sought are identified after development of the autoradiograph, and are then isolated and analysed by rapid preparation of plasmids.

(2) Rapid preparation of plasmid DNA

The plasmids are prepared from 1.5 ml of culture according to the alkaline lysis method of BIRNBOIM and DOLY (1979) modified by MANIATIS et al. (1982).

The plasmid DNA is analysed by digestion using restriction enzymes and fractionation on agarose gels.

III—PRODUCTION OF VIRAL PARTICLES BY TRANSFECTION OF CHICK FIBROBLASTS

The technique of transfection used is the calcium phosphate technique described by GRAHAM and VAN DER EB (1973) modified by WIGLER et al. (1977).

(A) Preparation of the DNA

The amount of DNA transfected per culture dish 60 mm in diameter is 10 to 15 µg. This DNA is composed of salmon sperm DNA (3 to 4 µg) and viral DNA. The viral DNA itself consists of the plasmid containing the modified AEV genome and the plasmid containing the DNA of the RAV-2 helper virus in a mole ratio of 5:1 to 10:1.

The DNA mixture is suspended in one volume of buffer A (25 mM HEPES, 250 mM $CaCl_2$, pH 7.15). The calcium phosphate precipitation is carried out by adding one volume of buffer B (25 mM HEPES, 280 mM NaCl, 1.5 mM $Na_2HPO_4$ pH 7.15) with rapid agitation (10 to 15 seconds). A very fine precipitate is observed in the mixture after 20 to 30 minutes at room temperature.

(B) Preparation of the Cells and Transfection $6 \times 10^5$ Chick embryo secondary fibroblasts are seeded in Petri dishes 60 mm in diameter 16 hours before transfection.

For the transfection, the precipitated DNA mixture is deposited in each culture dish and the cells are incubated for 5 to 6 hours at 37° C. The transfection medium is then replaced by fresh medium and the cells are suncultured in a Petri dish 100 mm in diameter. Every 3 to 4 days, each culture dish is subsequently distributed into 3 dishes 100 mm in diameter.

EXAMPLE 1

Clone of the Helper Virus DNA

The genome of the RAV-2 helper virus was obtained by BOONE and SKALKA (1981). It consists of an 8 kb sequence inserted at the SalI site of lambda phage DNA. This sequence was subcloned in plasmid pBR322 to provide the clone pRAV2. The RAV2 genome has a single SalI site situated in the env gene. For this reason, in the plasmid, the genome sequences are partially interchanged (FIG. 3).

In order to produce RAV-2 virions, the pRAV2 DNA has to be transfected on chick fibroblasts. The viral DNA has to be introduced into the receptor cells in the form of a genome enclosed by LTR and in which the arrangement of the genes corresponds to that existing in the viral RNA. This arrangement can be produced "in vitro" after digestion of plasmid pRAV2 with SalI, and religation with each other of the fragments obtained in order to create concatemers (FIG. 4).

Concatemerisation by ligation enables a number of molecules to be generated which may be integrated in the genome of the host cells and may transcribe genomic RNA capable of generating infectious virions. It will be noted that only a proportion of the concatemers is capable of giving rise to virions.

Thus, if only the dimer arrangement, which is essential for ensuring that the system operates, is considered, it is calculated that only ⅓ of the molecules will possess the structure of a reconstituted proviral genome.

EXAMPLE 2

Clone of Wild-Type AEV DNA

(a) pAEV11 clone

The starting clone consists of plasmid pAEV11 isolated by VENNSTROM et al. (1980), which is shown in FIG. 2a.

This clone consists of plasmid pBR313 in which the AEV genome of approximately 5.4 kb has been inserted at the single EcoRI site. In this clone, the viral genome shows an interchange due to the presence of the EcoRI site situated 37 pb upstream of the v-erbB termination codon. It should be emphasised that this clone contains a double LTR structure.

As in the case of pRAV2, the production of virions from pAEV11 involves the transfection, into chick fibroblasts, of concatemers which reconstitute a whole genome. In this case also, the proportion of concatemers having the favourable arrangement is low. In order to increase the efficiency of viral production by transfection, a clone in which the viral genome is reconstituted in a form identical to that of the provirus was recreated by "in vitro" genetic recombination.

(b) Construction of the clone pAEV2LTR

The rearrangement performed consists in isolating the 1.8 kb EcoRI-BamHI viral fragment (FIG. 5) covering the end of the v-erbB, the terminal 3' residue of the env gene (Δenv), the LTR sequences and the beginning of the gag gene. This fragment was inserted and cloned in pBR322 from which the EcoRI-BamHI minor fragment had been deleted. The plasmid obtained is known as pJS21.

The whole AEV genome is isolated from pBR313 after digestion of plasmid pAEV11 with EcoRI. The fragment carrying the AEV genome is ligated to plasmid pJS21 which has been opened beforehand at the single EcoRI site. One of the recombinants obtained, known as pAEV2LTR, has the structure of a provirus with an LTR copy at each end.

The pAEV2LTR DNA can be transfected into chick fibroblasts without prior digestion. After cotransfection with the DNA carrying the RAV2 helper virus sequences, the fibroblasts produce virions of the AEV type, and undergo oncogenic transformation discernible approximately 15 days after transfection. It is noted that the transfection with pAEV2LTR increases very distinctly the efficiency of viral production, relative to transfection with concatemerised pAEV11.

Thus, to induce the oncogenic transformation of a fibroblast culture, approximately 25 µg of concatemerised pAEV11 are necessary, whereas the same result is obtained with 10 µg of pAEV2LTR. Furthermore, the oncogenic transformation of the fibroblasts transfected with pAEV2LTR appears much more quickly than with concatemerised AEV11.

EXAMPLE 3

Insertion of the Human delta-Globin Gene into the AEV Genome

(a) Nature of the fragment inserted

The delta-globin fragment is obtained after digestion of plasmid pBRdeltaPst (FIG. 6) with EcoRI and isolation on a sucrose gradient. This DNA fragment begins upstream with a sequence derived from plasmid pBR322 (EcoRI-PstI, approximately 0.750 kb). The pBR fragment is maintained essentially with the object of retaining an EcoRI site at the 5' end of the delta fragment.

The specific structure of the delta region extends from the PstI site to the EcoRI site. In this sequence, the actual delta gene begins 460 bp downstream of the PstI site. This site, known as "cap" is the point of initiation of the transcription of the delta messenger RNA molecules. 30 bp upstream of the cap site, there is the sequence CATAAAAG, which is the homologue of the "TATA" sequence. Whereas the homologue of the second "CAT" consensus sequence encountered in the majority of eukaryotic genes between 70 and 80 bp upstream of the cap site appears to be modified in the case of the delta gene (AACCAAC). The two consensus sequences TATA and CAT are involved in the regulation of the transcription of the eukaryotic genes transcribed by RNA polymerase II. The transcribed region comprises, respectively, proceeding from the cap site from 5' to 3':
- a leader sequence covering 50 bp,
- the first exon (93 bp),
- the first intron (128 bp),
- the second exon (221 bp),
- the second intron (889 bp), and
- the first fifty base pairs of the third exon.

In consequence, the 3' end of the gene is curtailed from the EcoRI site. The consequence of this deletion is the removal of 75 bp of the 3rd exon and of the entire non-coding 3' region carrying, inter alia, the polyadenylation signal (AAUAAA) situated 18 bp before the transcription termination site.

(b) Cloning of the pBRdeltaEcoRI fragment in pAEV2LTR

The combination of the pBR and delta sequences gives rise to a 2.6 kb EcoRI-EcoRI fragment which is inserted in one of the EcoRI sites of pAEV2LTR. The identification of the pAEV2LTR clones which have undergone this insertion was carried out by the technique of transferring the bacterial colonies to a filter. Only the colonies which show positive hybridisation with both the delta-globin DNA probe and the gag-erbA DNA prove are adopted. Of 800 colonies analysed, 24 met these criteria. The insertion site and orientation site of the delta fragment are then determined by restriction mapping of the plasmids present in these positive bacteria.

Among the many possible combinations, only the recombinant plasmids which had inserted the globin gene at the EcoRI site situated at the end of the v-erbB gene, in both possible orientations, were adopted (FIG. 7). These recombinants are known as pAEV2LTRdelta(28) in the case where the direction of transcription of the gene is oriented in the same direction as that of the virus, and pAEV2LTRdelta(17) in the case of the reverse orientation.

Of the 24 clones which incorporated the fragment, two were of the pAEV2LTRdelta(28) type and four were of the pAEV2LTRdelta(17) type. The pAEV2LTR-delta clones hence possessed three EcoRI sites which we shall identify from left to right, respectively, by the names: EcoRI(1), EcoRI(2) and EcoRI(3).

(c) Structure of plasmid pAEV2LTRdelta(28)

Insertion of the fragment carrying the delta gene at the single EcoRI site of AEV interrupts the normal structure of the v-erbB gene (FIG. 8a). The result of this insertion is the creation of a new termination codon (UGA) for the ErbB protein, situated 1 bp downstream of the ECORI(2) site. In consequence, the erbB protein of the AEVdelta(28) mutant must have 12 amino acids less in the C-terminal region.

Since the signals for stopping transcription and for polyadenylation have been eliminated in the inserted PstI-EcoRI fragment, the viral structures localised in the right LTR sequence will probably have to fulfill these functions.

(d) Structure of plasmid pAEV2LTRdelta(17)

Insertion of the delta fragment in the reverse direction to that of the transcription of the virus brings about, in this case also, a shifting of the reading phase 75 of the v-erbB gene. A new termination codon is created bp downstream of the EcoRI site (FIG. 8b). As a result, the erbB protein of this mutant should theoretically contain, in the C-terminal region, 72 more amino acids than the erbB protein of the wild-type virus. In this recombinant viral genome, the viral strand which transcribes the genomic RNA (+strand) carries the anticoding strand of the delta gene. In this arrangement, the anticoding strand of the delta gene causes two sequences which recall the polyadenylation signals (AAUAAA) to appear 93 bp and 800 bp downstream of the EcoRI(2) site (FIG. 9b). In this construction, the promoter specific to the gene situated upstream of the cap site is no longer carried on the transcribed viral strand.

EXAMPLE 4

Characterisation of the Different Vectors

All the recombinant plasmids obtained by "in vitro" recombination are characterised by restriction mapping and hybridisation with a specific probe for the delta-globin gene. The plasmid DNA molecules of the different clones adopted, pAEV2LTR, pAEV2LTRdelta(28), pAEV2LTRdelta(17), are prepared by the alkaline lysis technique (MANIATIS et al. 1982), and digested, respectively, with the following 4 restriction enzymes: EcoRI, BamHI, PstI and SalI. The digestion fragments are separated on agarose gel and visualised in UV light. The DNA is then denatured in the gel and then transferred to a filter. The filter is hybridised with a deltaPst probe labelled with $^{32}P$ by nick translation. The bands corresponding to the fragments carrying the gene are revealed by exposure for autoradiography. For each recombinant, the sizes of the fragments resulting from the 4 digestions (EcoRI, BamHI, PstI and SalI) are deduced from the sizes of the fragments of the molecular weight marker used (lambda phage DNA digested with HindIII).

From these analyses, it is found that:
(1) the sizes of the fragments resulting from the various digestions agree for each recombinant with the expected sizes;
(2) hybridisation with the deltaPst probe reveals only the fragments carrying the delta sequence, in this case also being of the sizes expected.

From these two findings, it may be concluded that the recombinant clones adopted conform to the constructions sought.

EXAMPLE 5

Transfer of the delta-Globin Gene by AEVdeltas(28) and AEvdelta(17) Viral Particles (A) Production of Virus (1) Transfection of the proviral DNA into chick fibroblasts To determine whether the constructed recombinant vectors produce transmissible viruses, the recombinant plasmid pAEV2LTR and its derivatives pAEV2LTRdelta(28) and pAEV2LTRdelta(17) were transfected separately in the presence of DNA of the helper virus (pRAV2) into secondary cultures of chick embryo fibroblasts.

Cells were maintained in liquid medium and subcultured at regular intervals. The morphological change characteristic of the transformation of the fibroblasts by AEV appeared from the 4th passage (2nd week) for the three viruses. After being seeded in soft agar, these cells produce colonies of transformed fibroblasts. Supernatants of the transformed cultures were recovered in order to form stocks of virus and used for infecting fresh secondary fibroblasts, in which they induced oncogenic transformation visible at the end of approximately one week. This shows that viral particles were produced by the cells transfected with the DNA of recombinant viruses, and these particles are infectious and have retained their oncogenic power. The viruses produced, respectively, from plasmids pAEV2LTRdelta(17) and pAEV2LTRdelta(28) will be referred to as AEVdelta(17) and AEVdelta(28).

(2) Titration of the recovered viruses

The stocks of AEVdelta(17) and AEVdelta(28) virus were titrated for their transforming power according to the technique of counting foci of transformation. For this purpose, 1ml of diluted viral suspension was inoculated on cultures of fresh fibroblasts. The cultures are then covered with agar in order to enable foci of transformation to develop. The titre of the virus is given by the number of foci of transformation per dish multiplied by the dilution of the suspension of inoculated virus. The titre is expressed in FFU (focus forming unit) per ml.

The AEVdelta(28) virus recovered from the transfected cells had a titre of $5 \times 10^4$ FFU/ml, greater than that of the AEVdelta(17) virus ($2 \times 10^4$ FFU/ml).

The wild-type AEVwt virus, produced under similar conditions, generally has a titre in the region of $5 \times 10^5$ FFU/ml.

In order to verify the stability of the recombinant viruses, the viruses are maintained on chick fibroblast cultures for variable periods. For this purpose, the original stocks derived from the transfected cultures were inoculated into cultures of fresh fibroblasts which then underwent two subculturings, at the end of which the culture supernatants were collected to form the viral stocks II. The viruses of the stocks II were then propagated again on fresh fibroblasts during two subculturings, at the end of which the viral stock III was collected.

The titres of the viruses of the stocks II and III were determined and are shown in Table I.

TABLE I

| VIRAL STOCK | NUMBER OF TRANSFORMING VIRAL PARTICLES PER ML | |
|---|---|---|
| | AEVdelta(28) | AEVdelta(17) |
| Original I | $5 \times 10^4$ | $2 \times 10^4$ |
| II | $2 \times 10^4$ | $1 \times 10^4$ |
| III | $2 \times 10^4$ | $0.7 \times 10^4$ |

In general, a reduction in the titre of the virus during successive passages is observed. Although AEVwt was not tested in parallel, experience of the use of this virus shows that its titre remains substantially stable after several passages in cell cultures.

(B) Analysis of the Viral RNA Transcribed in the Infected Cells and Encapsidated in the Virions Chick embryo fibroblasts were infected with AEVwt, AEVdelta(17) and AEVdelta(28) viruses. When the cultures showed that a majority of cells were transformed, the culture supernatants and the cells were recovered separately.

From the supernatants, virions were collected by centrifugation. The RNA was extracted, respectively, from the virions and the cells. The cellular RNA was separated on oligo(dT)-cellulose into poly(A)+ and poly(A)− RNA. The cellular poly(A)+ RNA and the total RNA of the virions were fractionated by electrophoresis on agarose and transferred to a nitrocellulose filter. The filters were hybridised successively with different probes shown in FIG. 9. After exposure for autoradiography and development, the sizes of the bands observed were as summarised in Table II.

TABLE II

| VIRUSES | PROBES | | | | |
|---|---|---|---|---|---|
| | erbA | erbB | deltaPst | intron2delta | pBR |
| AEVwt | 5.3* | 5.3* | — | — | — |
| | — | 3.2 | — | — | — |
| AEVdelta(17) | 8 | 8 | 8 | 8 | 8 |
| (reverse insertion) | 6.3* | 6.3* | 6.3* | 6.3* | 6.3* |
| | — | 5.9 | 5.9 | 5.9 | — |
| | — | 4 | 4 | 4 | 4 |
| | — | 3.7 | 3.7 | 3.7 | — |
| AEVdelta(28) | 7* | 7* | 7* | — | 7* |
| (direct insertion | 5.2–4.8* | 5.2–4.8* | 5–4.8 | — | 5–4.8 |
| | — | 3 | — | — | — |
| | — | 2.8 | — | — | — |

The Table gives the sizes of the bands identified by the different probes in the fibroblasts infected with AEVwt, AEVdelta(17) and AEvdelta(28). The values indicated by an asterisk (*) correspond to transcripts present both in the cellular poly(A)+ RNA and in the RNA of the virions.

This Table demonstrates the production of virions carrying the RNA of the human delta-globin gene, as well as a portion of the RNA corresponding to the plasmid vector pBR.

(C) Analysis of the Proviruses Integrated in Fibroblasts Infected with the Recombinant Viruses (1) Object of the investigation of the proviral DNA With the exception of the LTR, the proviral DNA represents a perfect copy of the genomic RNA from which it is synthesised. Analysis of the provirus should hence provide data on the structure of the viral genome transferred into these cells. This analysis applied to the AEVdelta(17) and AEVdelta(28) mutants should enable it to be verified whether these viruses are capable of transferring, into the DNA of the infected cells, the genes which have been grafted into their genome. It also makes it possible to know whether these genes are transmitted integrally or whether structural modifications took place during the various cycles of development of the viruses.

(2) Identification of the proviral DNA sequences

The existence in chick fibroblast DNA of c-erb sequences related to the viral oncogenic sequences is revealed after hybridisation with probes of viral origin. These c-erb sequences are distinguished from the v-erb sequences by their restriction mapping.

(3) Analysis of the proviruses

Chick embryo fibroblast cultures were infected separately with AEVwt, AEVdelta(17) and AEVdelta(28). After the appearance of the transformed phenotype, the cells are trypsinised and lysed to extract their total DNA. The DNA is purified and digested with the restriction enzymes EcoRI or BamHI. The digestion products were separated on agarose gel, denatured and then transferred to filters. The filters were hybridised successively with erbB and deltaPst probes. Bands were revealed after 5 to 10 days' exposure for autoradiography. The bands corresponding to the AEVdelta(17) and AEVdelta(28) proviral genomes are identified by comparison with the DNA diagrams originating from cells infected with AEVwt.

(D) Interpretation of the Results: Structure of the Proviruses and Transcription of the Viral RNA The sizes of the characteristic bands from each provirus have been summarised in Table IV. The interpretation of these bands can be carried out by considering the restriction mapping of the proviruses shown in FIG. 10. Table III shows the theoretical size of the bands expected from the viral genomes which have been constructed. For the AEVdelta(28) virus, it has been considered that the intron2 of the delta gene has been removed.

TABLE III

THEORETICAL SIZES (kb) OF THE FRAGMENTS OBTAINED AFTER DIGESTION OF THE AEVdelta(17) AND AEVdelta(28) PROVIRUSES EITHER WITH BamHI, OR WITH EcoRI, AND RECOGNIZED BY THE VIRAL PROBES erbB OR, FOR GLOBIN, deltaPst
[These sizes were calculated from plasmids pAEV2LTRdelta(28) and pAEV2LTRdelta(17). It was considered that the provirus has lost the intron2, and possibly the intron1, of the delta gene.]

| | | PROBES | |
|---|---|---|---|
| VIRUS | ENZYMES | erbB | deltaPst |
| AEVdelta(17) | EcoRI | — | 2.6 |
| | BamHI | 1.5 | 1.5 |
| AEVdelta(28) | EcoRI | — | 1.5–1.6 |
| | BamHI | 2.2 | 2.2 |

TABLE IV

SIZES (kb) OF THE DNA OF THE AEVdelta(17) and AEVdelta(28) PROVIRUSES AFTER RESTRICTION MAPPING (FIG. 10)
[Values indicated by an asterisk (*) correspond to the sizes of the fragments expected after digestion with EcoRI and with BamHI].

| | | SIZES (kb) PROBES | |
|---|---|---|---|
| PROVIRUS | ENZYMES | erbA | erbB |
| AEVdelta(17) | EcoRI | — | 2.6* 1.4 |

TABLE IV-continued

SIZES (kb) OF THE DNA OF THE AEVdelta(17) and AEVdelta(28) PROVIRUSES AFTER RESTRICTION MAPPING (FIG. 10)
[Values indicated by an asterisk (*) correspond to the sizes of the fragments expected after digestion with EcoRI and with BamHI].

| | | SIZES (kb) PROBES | |
|---|---|---|---|
| PROVIRUS | ENZYMES | erbA | erbB |
| | BamHI | 1.5* | 1.5* |
| AEVdelta(28) | EcoRI | — | — |
| | BamHI | 2.2* 2.1* | 2.2* 2.1* |

The correlations between these two tables demonstrate the presence of provirus DNA segments containing human delta-globin sequences.

From the AEV genome cloned in the plasmid, an AEV genome containing human delta-globin gene sequences has hence been constructed by "in vitro" genetic recombination. After transfection of the recombinant viral DNA into chick fibroblasts in culture, infectious virions are obtained which contain a viral genome carrying the human delta sequences. After infection of fresh chick fibroblasts with these virions, it is observed that the cells integrate into their genome new genetic information represented by the human delta-globin gene.

EXAMPLE 6

Stability of the Transferred Genes (1) Removal of the introns from the transferred genes When the delta gene is inserted in the viral DNA, in an orientation such that the coding strand of the delta gene coincides with the viral coding strand, a more or less rapid loss of the introns of the delta gene is observed, which leads to the stabilisation of the viral genomes no longer carrying the delta coding sequences.

The loss of the introns is not observed when the delta gene is inserted in reverse orientation in the AEV genome. It must be concluded from this that the introns are probably removed by classical splicing phenomena in viral RNA molecules which are transcribed during successive cycles of viral infection.

(2) Size of the encapsidated genomes

The AEVdelta(28) virions can encapsidate a 7 kb genome whereas the AEVwt genome only represents 5.4 kb. This experiment shows that it is possible to transfer sequences of at least 1.6 kb by means of this vector. It is found that, in AEVdelta(17) virions, the 8 kb genomic RNA is not discernible. This defect of encapsidation can result, either from an excessively large size of the viral genome, or from a modification in the secondary structure of the viral genome due to the presence of the delta gene.

(3) Stability of the transferred genes

When the delta gene is inserted in the direct orientation, no major modifications are detected at the level of the coding sequences of this gene in the proviruses integrated in the infected cells.

After infection with AEVdelta(17), the integration is observed of provirus showing more or less substantial modifications in the 5' region of the delta gene and in the flanking pBR sequences.

Example 7- Selection of Viruses for Their Transforming Power-Functional Domain of the Protein Encoded by v-erbB The viruses generated from plasmids pAEV2LT-Rdelta(17) and pAEV2LTRdelta(28) induce the oncogenic transformation of chick fibroblasts "in vitro". In the AEVdelta(17) viral stock, the only genomes detected contain at least one portion of the inserted pBR and delta sequences. These viruses give rise to an erbB protein containing, in the C-terminal region, 24 amino acids more than the wild-type protein. This mutation hence does not affect the transforming power of the erbB gene product.

In the AEVdelta(28) viral stock, an abundance is found of a recombinant viral genome which has retained the pBR sequences and the coding sequences of the delta gene. The presence cannot be ruled out of genomes in which these sequences have been deleted and the structure of which would resemble that of the wild-type genome. The persistence of the recombinant genome in some virions suggests that these virions benefit from a selective advantage of production which might be linked to their oncogenic power. In these recombinant genomes, the v-erbB gene shows, relative to the wild-type gene, a structural modification which causes premature stopping of the translation of the protein (FIG. 8). The erbB protein produced by AEVdelta(28) does not contain the 12 C-terminal amino acids normally observed in the wild-type protein. If AEVdelta(28) is capable of transforming fibroblasts "in vitro", it must be concluded from this that these 12 C-terminal amino acids do not play an essential role in the transforming power of the erbB protein.

These observations show that it is possible to insert foreign nucleotide sequences at the EcoRI site of the v-erbB gene while still retaining the oncogenic and selective power of the virus.

In the AEVdelta(17) and AEVdelta(28) genomes, the delta gene is associated with its own sequences containing, in particular, the transcription control signals. In the two types of provirus, initiation of transcription is not observed at the level of the gene promoter. All the transcripts appear to be initiated at the level of the viral promoter situated in the left LTR.

To explain these results, several hypotheses can be put forward, among which the following three will principally be adopted:

(1) The delta-globin gene is expressed to only a small extent in human erythrocytes, and it is conceivable that its promoter is of low activity.

(2) Transcription from the proviruses has been analysed in fibroblasts in which the endogenous globin genes are not normally transcribed.

(3) Recent studies by CULLEN et al. (1984) show that the functional left LTR of a provirus exerts an inhibitory effect on the initiation of transcription from a promoter situated in proximity downstream. This phenomenon may be thought to be identical to that which we observe in the AEVdelta(28) provirus.

The examples which follow relate to non-oncogenic vector viruses, and the materials and methods employed are slightly different from those employed in the above examples.

MATERIALS AND METHODS

(1) Subclones of AEV DNA

A SalI-BamHI fragment (1.2 kb) which covers the region situated between v-erbA and v-erbB genes is inserted between the SalI and BamHI sites of plasmid pBR322. The structure of this clone (perb1) is shown in FIG. 11.

The clone pJS21 results from the cloning of an EcoRI-BamHI fragment (1.8 kb) which covers the viral 5' region of pAEV11, between the EcoRI and BamHI sites of pBR322 (FIG. 12).

The recombinant pAG50 was constructed by COLBERE-GARAPIN et al. (1981). It contains a BglII-HincII fragment (1.1 kb) derived from the prokaryotic transposon Tn5 in which the structural gene for resistance to neomycin, Neo$^r$, is present, devoid of its own promoter (FIG. 13) (BECK et al. 1982).

(2) Digestion of the DNA with Restriction Enzymes

The digestion of the DNA with restriction enzymes is carried out as described earlier. In some cases, the digested DNA is purified by extraction with phenol/chloroform and then with a chloroform/isoamyl alcohol mixture, and then precipitated with ethanol.

(3) Technique of Digestion of the DNA with Bal31 Nuclease

Bal31 nuclease progressively degrades linear double-stranded DNA from the 5' and 3' ends of each strand. Given a defined amount of DNA, the rate of digestion can be controlled in terms of the concentration of Bal31, the reaction temperature and the incubation time. Specificity of Bal31 enables us to remove successively the nucleotide sequence within which the usable restriction sites are absent.

12 μg of the perb1 DNA linearised with BamHI are incubated at 30° C. in the presence of an incubation buffer containing 12 mM CaCl$_2$, 12 mM MgCl$_2$, 600 mM NaCl, 20 mM Tris HCl (pH 8), 1 mM EDTA and 2.2 units of Bal31. Aliquots (2 μg) are withdrawn after 5, 10, 15, 20, 25 and 30 minutes, respectively. The enzyme is inactivated by adding a solution containing 0.5% SDS and 25 mM EDTA. The digested DNA is then treated with phenol, precipitated with cold absolute alcohol and then subjected to digestion with SalI, and is finally analysed by electrophoresis on a 1.6% agarose gel. From the kinetics obtained for this reaction, the rate of degradation of a molecule is approximately 30 nucleotides per minute.

Based on the preliminary test, 25 μg of perb1 DNA are subjected to digestion with Bal31 under the conditions described above for 15 minutes. The digested DNA is then purified and the ends are then repaired by the "Klenow" fragment derived from E. coli DNA polymerase I, in the presence of the 4 nucleotide triphosphates (dATP, TTP, dCTP, dGTP).

(4) Isolation of the DNA Fragments of Different Sizes

The mixture of the DNA fragments of variable sizes is first redissolved in double-distilled water so as to obtain a concentration of 100 μg of DNA per ml. Electrophoretic separation is then carried out at 30 volts overnight (16 hours) on horizontal preparative agarose gel, the concentration of which varies from 0.8 to 1.6% according to the sizes of the fragments to be separated. Molecular weight markers, in general either of lambda bacteriophage DNA digested with the restriction endonuclease HindIII or plasmid pBR322 DNA digested with the restriction endonuclease AluI, are subjected to electrophoresis in parallel with the samples. Staining of the gel with ethidium bromide enables the DNA bands to be visualised under ultraviolet light. The region of the gel containing the band of DNA fragments of specified sizes is cut out. The DNA is then eluted by the "freeze-squeeze" method. This procedure leads to the production of DNA ready to be subjected to ligation or to digestion with restriction enzymes.

(5) Ligation of the DNA Fragments and Cloning Vectors

Ligation of the isolated DNA fragments and vector DNA is carried out according to the technique described above.

(6) Cloning and Selection of the Recombinant Plasmids

Transformation of the bacteria, selection of the bacteria and rapid analysis of the plasmids are carried out according to the techniques described above.

(7) Preparation of the Plasmid DNA

The plasmid DNA is isolated on a cesium chloride gradient as described above.

In some cases, this DNA is subsequently purified on an NaCl cushion in order to remove the contaminant oligoribonucleotides (MANIATIS 1982).

(8) Sequencing

The fragments to be sequenced are cloned in the variants mp8 and mp11 of phage M13. Sequencing of the fragments is carried out according to the method of SANGER et al., 1977.

(9) Attachment of Synthetic Linker Oligonucleotides

In cases where a restriction site compatible with the cohesive ends of the DNA fragment to be cloned is absent, the use of synthetic linker oligonucleotides containing the restriction site sequence enables new cloning sites to be created in these vectors.

(9.1) Phosphorylation of the linkers

To introduce a BglII restriction site in the vector pXJ4 (FIG. 14), the BglII linkers 5-d(CAGA-TCTG)-3' (BRL) are chosen.

3 µg of BglII linkers are phosphorylated at 37° C. for 30 minutes in the presence of 100 µl of a solution composed of 1 µM cold ATP, 30 µCi of (gamma-$^{32}$P)ATP (5,000 µCi/mole), a buffer containing 60 mM Tris-HCl (pH 7.8), 10 mM MgCl$_2$ and 15 mM 2-mercaptoethanol, and 80 units of phage T4 polynucleotide kinase (BRL). The phosphorylate linkers are then subjected to various controls related to checking their capacity to bind in the presence of phage T4 ligase and to be digested by the restriction enzyme BglII.

(9.2) Modification of the emergent 5' cohesive ends

The digestion of the DNA with some restriction endonucleases leads to the production of molecules bearing emergent 5' cohesive ends. To ligate the vector arms bearing the emergent 5' cohesive ends with the blunt-ended linkers, it is hence essential to convert the cohesive ends to blunt ends.

17.5 µg of pXJ4 linearised with the restriction enzyme EcoRI are incubated at 25° C. for 10 minutes in the presence of 39 units of the "Klenow" fragment derived from E. coli DNA polymerase I (BRL), an incubation buffer containing 50 mM Tris-HCl (pH 7.4), 10 mM MgSO$_4$, 0.1 mM DTT and 50 µg of bovine serum albumin per ml, $3.9 \times 10^{-2}$ mM of cold nucleotide triphosphates (dATP, dCTP, dGAP) and 40 µCi of (32P)TTP. After 10 minutes, 10 µl of 2 mM cold TTP are added in 515 µl of reaction medium, and the incubation is continued for 10 minutes. The modified DNA is subsequently purified by extraction with phenol and precipitated with cold ethanol.

(9.3) Insertion of the linkers into the vectors

The molecular ratio between the linkers and the vectors to be ligated is generally greater than 50:1. 750 µg of pXJ4 DNA and 570 ng of BglII linkers are incubated at 15° C. for 20 hours in the presence of 5 units of phage T4 ligase and a ligation buffer identical to that described in Section II (c), in a final volume of 60 µl.

To remove the excess linkers, the ligation reaction medium is then incubated in the presence of the restriction enzyme BglII. The linearised DNA is then subjected to two precipitations at −80° C. for 30 minutes in the presence of a mixture of ethanol and 1.5M ammonium acetate. These two precipitations enable the high molecular weight DNA (vectors) to be recovered by centrifugation, while the free and digested linkers remain in the supernatant. The vectors thus modified are then religated and cloned in C600 bacteria. The introduction of a BglII site is identified by restriction mapping.

(10) Transection of Eukaryotic Cells (10.1) Culturing the cells

Cells used for the transfection are as follows: mouse L cells (continuous line), quail QT6 cells (continuous line) and chick embryo fibroblasts CEF.

Culturing of the mouse L cells and the chick embryo fibroblasts is carried out according to the techniques described above.

The quail QT6 cells are cultured at 37° C. in MEM medium (Gibco) containing 2.5 mg/ml of TPB (tryptose phosphate broth), 10% of foetal calf serum, 1% of chicken serum, 0.19% of sodium bicarbonate, 100 units of penicillin per ml, 100 µg of streptomycin per ml, non-essential aminoacids, vitamins, 4 mM glutamine and 1% of DMSO (dimethyl sulphoxide).

These cells are cultured at 37° C. in a moist atmosphere containing 5% of CO$_2$.

(10.2) Transfection of the cells by the calcium phosphate method

The technique is identical to that described above.

(10.3) Transfection of the cells by the Polybrene/DMSO method

The principle of this method is based on the fact that the presence of polycations (Polybrene) leads to the attachment of DNA to the cell membranes. Penetration of the DNA into the cells is facilitated by treating the cells with DMSO (dimethyl sulphoxide), which increases the permeability of the cell membranes (KAWAI et al. 1984).

$5 \times 10^5$ mouse L cells are seeded in a Petri dish of diameter 60 mm. After 16 hours' incubation, the cells are brought into contact with 4 µg of transforming DNA and incubated at 37° C. in the presence of one ml of fresh culture medium containing 25 µg of Polybrene.

After 6 hours, the cells are treated with 2 ml of fresh culture medium containing 25% of DMSO at 37° C. for 4 minutes.

(10.4) Selection of the transformed cells in the presence of G418

2 to 4 days after transfection, the cell was subjected to selection in the presence of the antibiotic G418, the concentration of which is 800 μg/ml of culture for the mouse L cells, 400 μg/ml of culture for the QT6 cells and 300 μg/ml for the chick fibroblasts.

EXAMPLE 8

Localisation of the 5' Region of the AEV-R erbB Gene

In the AEV wild-type genome, the two viral oncogenes v-erbA and v-erbB occupy most of the coding regions (FIG. 15). A HincII-BamHI fragment (1.2 kb) contains the 3' region of the erbA gene, a non-coding sequence interposed between the v-erbA gene and the v-erbB gene, and the 5' region of the v-erbB gene. In order to determine the exact position of the v-erbB gene initiator codon and the splicing acceptor site situated between v-erbA and v-erbB, the nucleotide sequence of this region was determined. The HincII-BamHI fragment is first cloned in the vectors derived from bacteriophage M13, mp8 and mp11 (FIG. 16). In the single-stranded state, the "plus" strand of the fragment studied is present in the clone p42 derived from mp8, whereas the "minus" strand is in the clone p314 derived from mp11.

Sequencing performed on the clone p42 makes possible the determination of a portion of sequence of the 5' region of the v-erbB gene starting from the BamHI site (FIG. 17).

Comparison of the AEV v-erbB gene sequence and that of the v-erbB of the AEV-H variant supplied by YAMAMOTO et al., 1983, reveals a homology of 276 nucleotides out of 279. This substantial homology enables it to be deduced that, in the AEV genome, the distance between the BamHI site and the "AUG" initiator codon of the v-erbB gene measures 400 to 500 nucleotides, assuming that the two v-erbB genes are identical in their 5' sequences.

EXAMPLE 9

Removal of the Nucleotide Sequence of the 5' Region of the v-erbB Gene

In view of the absence of a usable restriction site upstream of the BamHI site in the 5' region of the v-erbB gene, nuclease Bal31 was employed for removal of this region, starting from the BamHI site.

The clone perb1 containing the junction sequences between v-erbA and v-erbB (FIG. 11) is digested with the restriction enzyme BamHI and then with nuclease Bal31, which brings about progressive degradation of the 5' region of the v-erbB gene from the BamHI site. The digestion is controlled in such a manner that a nucleotide sequence of approximately 0.45 kb is removed upstream of the BamHI site. Separation of the shortened viral fragments of vector pBR322 is carried out by digestion with the restriction enzyme SalI followed by preparative agarose gel electrophoresis.

A family of viral fragments, the sizes of which are in the region of 0.8 kb, is isolated from the gel. These fragments show a more or less extensive deletion in the 5' region of the v-erbB gene.

EXAMPLE 10

Structural Study of the Non-Coding Region Between the v-erbA and v-erbB Genes

To determine the deletion introduced in the 5' region of the v-erbB gene, the Bal31 shortened fragments are first cloned between the SalI and SmaI sites of mp11 (FIG. 11).

4 sequenced clones show longer or shorter residues of v-erbB sequence (FIG. 18).

Among all these clones, the clone p15-16 only retains the first 13 nucleotides of the v-erbB gene.

Analysis of the sequences upstream of the "ATG" codon of the v-erbB gene shows that there is a consensus "CAG" splicing acceptor site in position 171, preceded by sequence of 15 nucleotides "TTTCTTTCCTTTTTG" (FIG. 18) (SHARP, 1981).

The "TAG" termination codon of the v-erbA gene occurs 188 nucleotides upstream of the "ATG" codon of the v-erbB gene. Furthermore, the non-coding sequence is characterised by a high frequency of doublets and triplets of A nucleotides and T nucleotides, respectively.

A comparative study with the AEV-H sequence supplied by YAMAMOTO et al., 1983, shows that the sequences immediately downstream of the "ATG" codon of the v-erbB gene are virtually identical in AEV and AEV-H.

EXAMPLE 11

Construction of the Mutant pAEVΔerbB

With the object of replacing the v-erbB gene by a "marker" gene, the Neo$^r$ gene derived from the bacterial transposon Tn5 was inserted in the modified genome of AEV.

The strategy adopted in this construction is shown schematically in FIG. 12.

The clone p15-16 is first digested with the restriction enzymes EcoRI and SalI. A SalI-EcoRI fragment (0.75 kb), which covers the 5' region of the v-erbA gene, the non-coding sequence containing the splicing acceptor site, the first 13 nucleotides of the v-erbB gene and 11 nucleotides derived from the mp11 polylinker, is isolated by agarose gel electrophoresis. Double digestion of the pAEV124Ba clone with SalI and EcoRI enables a 3.1 kb fragment to be isolated containing, inter alia, the LTR sequences, the gag residual sequences and the 5' half of the AEV v-erbA gene.

These two fragments are ligated in tandem and cloned in the EcoRI site of plasmid pJS21, which provides the 3' viral sequences. The final plasmid containing a reconstituted viral genome, devoid of the v-erbB gene, is known as pXJ4. The structure of plasmid pXJ4 is confirmed by the results of digestion with SalI, SacI, PstI, BamHI and SalI+EcoRI.

EXAMPLE 12

Introduction of the Neo$^r$ Structural Gene of Tn5 into the Retroviral Vector pXJ4

Production of the retroviral vector pXJ4 offers the possibility of inserting a selection gene at the location of the deleted v-erbB gene without increasing the total size of the vector relative to that of wild-type AEV.

Plasmid pAG50, shown in FIG. 13, contains the structural gene for resistance to the antibiotic neomycin (Neo$^r$ gene) bounded by BglII sites (COLBERE- GARAPIN et al., 1981). Digestion of pAG50 with BglII enables a 1.2 kb fragment to be isolated containing the Neo' gene.

To introduce this fragment into plasmid pXJ4 at the location of the deleted v-erbB gene, a BglII restriction site had to be created in plasmid pXJ4 at the level of the EcoRI site situated downstream of the splicing acceptor site. Plasmid pXJ4 was subjected to partial digestion with EcoRI, and the linearised 9.7 kb molecules resulting from a single cut with EcoRI were then isolated on preparative agarose gel. The ends of the isolated fragments were then repaired to form square ends and then linked to BglII linkers.

This procedure gives rise to EcoRI sites enclosing the BglII site created (FIG. 14). The genome thereby produced is represented by plasmid pXJ5 (FIG. 14).

The digestion of pJX5 with BglII proves that there has been insertion of a BglII site. Double digestions with BglII and SacI, or BglII and SalI, confirm the position of this site downstream of the residual "AUG" initiator codon of the v-erbB gene. The restoration of the EcoRI site is confirmed by digestion with EcoRI.

Insertion of the Neo' gene in the vector pJX5 is carried out by the following procedure: plasmid pXJ5 is first linearised at the BglII site and then linked with the BglII-BglII fragment containing the Neo' gene isolated from pAG50.

Analysis of the recombinant clones shows that the clone pXJ1 contains a single copy of the Neo' gene inserted in the same transcriptional orientation as that of the retroviral vector (FIG. 19). The clone pXJ2 (FIG. 20) carries a single copy of the Neo' gene, the orientation of which is opposite to that of the vector. The clone pXJ3 (FIG. 21) possesses two copies of the Neo' gene joined in tandem, both oriented in the direction of transcription of the viral genome. The insertion sites and the number and orientation of the Neo' genes in plasmids pXJ1, pXJ2 and pXJ3 were determined by digesting the plasmids with each of the enzymes BglII, EcoRI, HincII and PstI.

The junction sequences between the Neo' gene and the retroviral vectors in the clones pXJ1 and pXJ3 are shown in FIG. 22.

EXAMPLE 13

Expression of the Neo' Gene in Procaryotic Cells

Bacteria of the Kan$^s$ type (kanamycin-sensitive) transformed by pXJ1, pXJ2 and pXJ3, are cultivated at 37° C. for 16 hours in the presence of a nutrient liquid medium containing kanamycin, the concentration of which varies from 0 to 600 µg/ml of culture. The bacteria transformed by the clone pXJ5 without a Neo' gene are also tested as a control.

In the presence of 50 µg of kanamycin per ml of culture, only the bacteria transformed by recombinants carrying the Neo' gene show normal growth. Nevertheless, when the concentration of kanamycin is greater than 50 ug/ml of culture, the bacteria harbouring the clones pXJ1 and pXJ3 show growth which is at least 10 times greater than that of the bacteria containing plasmid pXJ2. No difference in kanamycin sensitivity is observed between the bacteria which contain pXJ1 and those which contain pXJ3.

EXAMPLE 14

Expression of the Neo' Gene in Eukaryotic Cells (1) Transfection in the presence of calcium phosphate (1.1) Transfection of mouse L cells (Table V)

$5 \times 10^5$ mouse L cells are subjected to transfection by 15 µg of DNA of each of the vectors pXJ1, pXJ2 or pXJ3. Plasmid pAG50, in which the Neo' gene is under the instructions of the transcription control elements of the herpes simplex virus tk gene, is chosen as control (COLBERE-GARAPIN et al., 1981).

24 hours after transfection, the cells are selected in liquid medium in the presence of 800 µg of G418 per ml of culture. After 14 days of selection, the cells which have not undergone transfection, and also the cells transfected with plasmid pXJ2, are all dead. By contrast, the cells transfected with pXJ1 and pXJ3 survive and begin to form colonies. The numbers of resistant colonies are counted after 19 days of selection. The efficiency of transformation shown by the clone pXJ3 carrying two copies of the Neo' gene is less than that of the clone pXJ1 containing a single copy.

(1.2) Transfection of quail QT6 cells (Table V)

$5 \times 10^5$ quail QT6 cells are transfected with 5 µg of the retroviral vectors pXJ1, pXJ2 and pXJ3 respectively. In parallel, 15 µg of pAG50 are used as control. 25 hours after transfection, the cell was subjected to selection in liquid medium in the presence of 400 µg of G418 per ml of culture.

After 7 days of selection, the normal, nontransfected cells are all dead under a selection pressure of this kind. To facilitate the development of resistant colonies, concentration of G418 is lowered to 200 µg/ml. After continuous selection for 4 days, 33 resistant colonies are formed in the case of pXJ1, while the other clones show no transformation activity.

(1.3) Transfection of chick embryo fibroblasts (Table V)

$5 \times 10^5$ secondary chick embryo fibroblasts are transfected with 5 ug of the vectors pXJ1, pXJ2 and pXJ3, respectively. At the same time, 15 µg of pAG50 are employed as control. 6 days after transfection, the transfected cells are selected in liquid medium containing 300 µg of G418 per ml of culture. After two weeks of selection, the normal, non-transfected fibroblasts and also the fibroblasts transfected with pXJ2 and pAG50 are all dead. In contrast, the cells transfected with pXJ1 and pXJ3 begin to form colonies. The numbers of resistant colonies are counted following continuous selection for 3 days. The clone pXJ1 containing one copy of the Neo' gene yields about twice as many resistant colonies as the clone pXJ3. The fibroblasts transformed by the vectors pXJ1 and pXJ3 show a morphology identical to that of the normal cells.

(2) Transfection of mouse L cells in the presence of Polybrene (Table V)

$5 \times 10^5$ mouse L cells are transfected with 4 µg of each of pXJ1, pXJ2, pXJ3 and pAG50 transforming DNA. 48 hours after transfection, the cells are cultured in liquid medium containing 800 µg of G418 per ml of culture. After 12 days of selection, the normal, non-transfected cells and also the cells transfected with plasmids pXJ2 and pAG50 are all dead. In contrast, the clones pXJ1 and pXJ3 induce the development of resistant colonies.

The efficiency of the Polybrene/DMSO transfection method appears to be much higher than that of the calcium phosphate method.

TABLE V
TRANSFECTION OF EUCARYOTIC CELLS WITH RETROVIRAL VECTORS

| Clone | Structure | DNA (μg) | Number of transformed colonies | Method of transfection |
|---|---|---|---|---|
| Number of mouse L cells: 5 × 10⁵. Selection in presence of G418 800 μg/ml ||||||
| pXJ1 | LTR → neo$^T$ → LTR → | 15 | 19 | CaPO₄ |
| pXJ2 | LTR → neo$^r$ ← LTR → | 15 | 0 | |
| pXJ3 | LTR → neo$^r$ → neo$^T$ → LTR → | 15 | 17 | |
| pAG50 | tkbr → neo$^r$ → tkpolyA | 15 | 9 | |
| pXJ1 | LTR → neo$^T$ → LTR → | 4 | 32; 36 | POLYBRENE/DMSO |
| pXJ2 | LTR → neo$^r$ ← LTR → | 4 | 0; 0 | |
| pXJ3 | LTR → neo$^r$ → neo$^T$ → LTR → | 4 | 20; 24 | |
| pAG50 | tkbr → neo$^r$ → tkpolyA | 4 | 35; 32 | |
| 5 × 10⁵ quail QT6 cells. G418: 400 μg/ml ||||||
| pXJ1 | LTR → neo$^r$ → LTR → | 5 | 33 | CaPO₄ |
| pXJ2 | LTR → neo$^r$ ← LTR → | 5 | 0 | |
| pXJ3 | LTR → neo$^r$ → neo$^T$ → LTR → | 5 | 0 | |
| pAG50 | tkbr → neo$^r$ → tkpolyA | 5 | 0 | |
| 5 × 10⁵ chick embryo fibroblasts (CEF). G418: 300 μg/ml ||||||
| pXJ1 | LTR → neo$^T$ → LTR → | 5 | 7 | CaPO₄ |
| pXJ2 | LTR → neo$^r$ ← LTR → | 5 | 0 | |
| pXJ3 | LTR → neo$^r$ → neo$^T$ → LTR → | 5 | 3 | |
| pAG50 | tkbr → neo$^r$ → tkpolyA | 5 | 0 | |

The transcriptional organisation of the transforming DNA is shown in this table. The transcriptional orientation of each component is indicated by a horizontal arrow.
  tkpr: HSV tk gene promoter
  tkpolyA: polyadenylation signal of the HSV tk gene.

EXAMPLE 15

(1) Preparation of the clone mJS21 erb⁻ (FIG. 24)

This clone was prepared from the clone pJS21 (Example 2, FIG. 23) which contains, in addition to the sequences already described, about 40 nucleotides belonging to the erbB oncogene which are situated at the 5' site of the env gene. This residual sequence was removed by EcoRI linearisation and digestion with Bal31.

Fragments obtained are repaired with DNA polymerase I. The insert is released at the BamHI site by enzyme digestion and purified by electroelution after separation on agarose gel.

The purified fragments are then cloned in the replicative form of phage M13, which is prepared beforehand. After ligation and transformation of a competent JM103 bacterial culture, the recombinant single-stranded phages are analysed by hybridisation with a clone containing the JS21 fragment integrated in the reverse direction. The presumptive clones are then verified by sequencing.

The clone adopted, mJS21 erb−, begins in the env gene 9 nucleotides on the 3' side of the erbB gene terminator codon.

(2) Preparation of the clone mp11gag mp10gag erbA contains the last 400 nucleotides of the gag gene as well as the first 400 nucleotides of the erbA gene. In the same manner as for the clone mJS21 erb−, the erbA sequence of the clone mp10gag erbA was removed by digestion with the exonuclease Bal31 (FIG. 24).

In the adopted clone mp11gag, after analysis of the presumptive clones by sequencing, the erbA gene is completely removed together with 12 terminal 3' nucleotides of the gag gene.

(3) Preparation of the clone mp10J (FIG. 25)

The J fragment was prepared from the clone mp11 p15-16 (Example 10) (designated 15-16). The latter contains, in addition to the J sequence, the last 550 nucleotides of the erbA gene. After analysis of the sequence published by DEBUIRE et al. (1984) relating to this region of AEV, a single FokI restriction site was identified in proximity to the junction of the two sequences erbA and J. Thus, digestion of the DNA of the clone mp11 p15-16 with this endonuclease releases the J fragment. On the 5' side of J, there only remain 10 nucleotides of the coding sequence of the erbA gene.

EXAMPLE 16

Reconstruction of the Vector Devoid of Oncogenic Sequences

The assembling of the different clones obtained in Example 15 is carried out in the bacterial plasmid pBR328 (Bolivar et coll., 1977). The latter can, in effect, insert large fragments, and can be selected for its resistance to ampicillin.

(1) Cloning of the gag sequence of mp11gag in pBR328 (FIG. 26)

The first fragment introduced into the plasmid is that which contains the gag gene present in the clone mp11gag. Clone pBRgag thereby obtained is analysed by restriction endonuclease mapping.

(2) Preparation of the clone pBRgag-J (FIG. 27)

(a) Preparation of the vector pBRgag

The preparation of the vector pBRgag for insertion of the J fragment required a series of stages designed to preserve the EcoRI site situated on the 3' side of the gag sequence. This EcoRI site must, in effect, in the final construction, serve as a single cloning site for the genes to be inserted into the retroviral vector.

To prepare the vector pBRgag, T4 DNA polyerase is used in order to obtain blunt ends after digestion with the endonuclease SacI. The activity of this T4 DNA polymerase is not strictly controllable and, since the two enzyme sites used for this subcloning (SacI and EcoRI) belong to the phage M13 polylinker and are very close to each other, there is a risk of losing the EcoRI site. For this reason, in order to place the EcoRI site at a distance from the SacI site, a 2.7 kb DNA fragment belonging to the human gamma-globin gene is introduced into the vector pBRgag. This ingeneous technique makes it possible, after various stages, to preserve the EcoRI site.

(b) Preparation of the clone mp10-J

The J fragment, as prepared, is present in the vector mp10 between the SmaI and EcoRI sites of the polylinker. This causes 5 restriction sites (BamHI, XbaI, SalI, PstI and HindIII) to appear on the 5' side of the J fragment. Now, to continue the construction, the BamHI site has to be eliminated. This is achieved by digestion with the endonuclease BamHI, followed by filling-in using DNA polymerase I and ligation. After analysis by mapping of the replicative forms of phage M13, the presumptive clones are analysed by sequencing.

Clone mp10 thereby prepared is enclosed in pBRgag. After transformation of a competent C600 R/S bacterial culture, the pBRgag-J recombinant clones are analysed by mapping. Cloning of the J fragment in pBRgag creates the single XbaI site situated on the 5' side of J, which will be used for cloning the genes to be inserted in the vector.

(3) Cloning of the JS21 erb− fragment on the 3' side of J in the vector pBRgag-J (FIG. 28)

The vector pBRgag-J and the JS21 erb− fragment are separated as shown in the figure. Cloning of the JS21 erb− fragment on the 3' side of J provides the vector with the env gene sequence as well as the 3' LTR. It also creates the single EcoRI site which will be used for subcloning the genes to be inserted into the vector. Clones pBRgag-J env LTR thereby obtained are analysed by mapping.

(4) Cloning of the vector pBRgag-J env LTR in pJS21 (FIG. 29)

The pBRgag-J env LTR fragment and pJS21 are prepared as shown in the figure. This subcloning provides the vector with 5' LTR, the leader sequence, and enables the gag gene to be reconstituted as it exists in wildtype AEV. Clone pBRgag-J-env 2LTR thereby obtained is analysed by mapping.

It should be noted that this stage leads to the appearance of an additional EcoRI site situated at the junction of the AEV and pBR322 sequences. This will have to be removed subsequently by partial digestion in order to have only one EcoRI site situated on the 3' side of the J fragment, which will serve for cloning the genes to be inserted. This clone pBRgag-J-env 2LTR contains between the 2 LTR sequences the AEV genome without the oncogenic sequence, and it also possesses a single XbaI cloning site situated on the 5' side of the J fragment.

An XbaI restriction fragment of the transposon Tn5 including the Neo$^r$ gene is introduced in the XbaI site of the pBRgag-J-env 2LTR, and the resulting plasmid is pAEV TSN which induces resistance to G418 for the transformed avian cells.

EXAMPLE 17

Transfer of the Genes Under the Dependence of the Viral Promoter

In a first series of constructions, the Neo$^r$ gene of the bacterial transposon Tn5 was inserted in place of the v-erbB gene (Examples 12 et seq.). The viruses produced were able to induce the resistance of the infected cells to the drug G418, thereby showing that correct transcription and translation of the inserted gene had taken place. This construction, however, allowed several potential translation initiation codons to remain, in various reading frames, upstream of the Neo$^r$ gene coding sequence. In order to increase the efficiency of translation of the gene, and with the object of producing a universal transfer vector, the vector sequence was modified in order to leave remaining only the initiator codons normally used for the translation of the viral genes.

(a) Construction of a universal vector carrying an NdeI cloning site at the level of an ATG initiator codon (FIG. 30)

The coding region of the v-erbB gene has, on the 5' side, the following sequence:

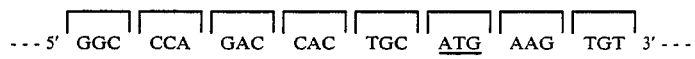

After splicing of the genmic RNA to subgenomic RNA, this sequence becomes arranged behind the leader sequence of the subgenomic RNA which carries the translation initiator codon. This arrangement yields the coding frame indicated above ( ⎡⎤ ).

An NdeI site covering the ATG codon was created by the directed point mutagenesis method, according to Zoller et al. (1983), using a synthetic oligonucleotide of sequence:

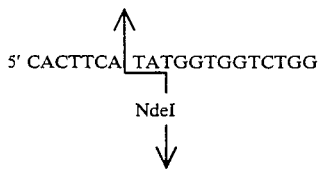

The sequence modification was carried out on the clone p15-16 (FIG. 12) to yield the clone pXJ17 in which the sequence on the 5' side of the v-erbB gene is now as follows:

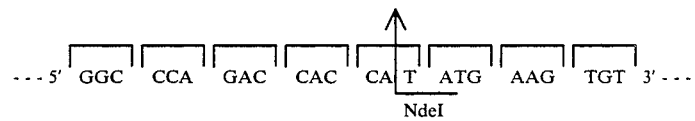

This sequence was inserted in the vector according to the construction shown in FIG. 30, to yield finally the vector viral genome carried by plasmid pXJ11, starting with pJS21 and pAEV124, the genome being obtained by PstI-PstI deletion in the v-erbA gene of pAEV11.

This clone hence offers a universal system for constructing vector genomes in which any sequence inserted at the NdeI cloning site will automatically be in phase with the protein translation frame initiated in the leader region of the transcribed viral RNA molecules. The genes to be integrated in these vectors will consequently have to contain an NdeI restriction site at the level of their initiator codon.

(b) Construction of a Neo$^r$ gene carrying an NdeI restriction site at the level of the initiator codon The nucleotide sequence in the 5' region of the Neo$^r$ gene is as follows:

This sequence was modified by directed point mutagenesis using a synthetic oligonucleotide of sequence:

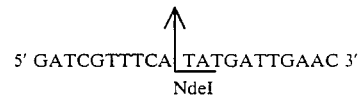

Plasmid pXJ10, containing the modified Neo$^r$ gene in which an NdeI site appears at the level of the initiator codon, was thereby constructed. The coding portion of the gene can be isolated from this plasmid after digestion with NdeI and BglII.

(c) Construction of a retroviral vector carrying the modified Neo$^r$ gene

The coding portion of the modified Neo$^r$ gene was inserted in plasmid pXJ11 at the level of the NdeI site, in such a manner that the Neo$^r$ sequence was in the normal direction of transcription of the viral genome. Plasmid pXJ12 was thereby obtained. The final structure of the plasmid and the viral genome was verified by restriction mapping, in particular to confirm the presence of the NdeI site and consequently the validity of the sequence in the region of the gene initiator codon. The structure of this plasmid is given in FIG. 31.

When transferred into bacteria, this plasmid induces the resistance to kanamycin at a concentration of 50 μg/ml. This plasmid thus constitutes a sort of shuttle vector, which can be selected both from bacteria in plasmid form and from avian cells in provirus form.

(d) Production of viruses derived from plasmid pXJ12

By cotransformation of the DNA from plasmid pXJ12 and DNA containing the genomes of helper virus RAV-1 or RAV-2 into chick fibroblasts, it was possible to recover AEV-XJ1 (RAV-1) and AEV-XJ12 (RAV-2) virions. These virions can infect chick fibroblasts in vitro and induce their resistance to the drug G418.

Virus AEV-XJ12 hence constitutes a selectable viral vector. The genes to be transferred may be inserted in the region still occupied by the v-erbA sequences.

(e) Expression of the viral genes in chick fibroblasts infected with the vectors AEV-XJ1 and AEV-XJ12

In order to verify whether the insertion of the Neo$^r$ gene in the viral genome does not adversely effect the mechanisms of transcription, analysis was performed of the RNA molecules produced in chick fibroblasts infected with the vectors AEV-XJ1 (vector containing several ATG sequences) and AEV-XJ12.

In these cells, two types of RNA are found, corresponding to the genomic and subgenomic RNA, which demonstrates that the maturation of the RNA molecules is correct. However, in the cells infected with AEV-XJ1, a predominance is observed of the subgenomic RNA which codes for the Neo$^r$ protein. The relative expressions of the genomic and subgenomic RNA molecules are not substantially different in the cells cultured in the presence or absence of G418. In contrast, in the fibroblasts infected with AEV-XJ12, substantially more genomic RNA is observed than subgenomic RNA, in a ratio which is identical to that observed for the wild-type AEV.

(f) Method of titration of avian viruses carrying the Neo$^r$ gene

The biological titration of viruses carrying a Neo$^r$ gene rests on the induction of resistance to G418 in infected cells. No standard method has hitherto been proposed for avian viruses. A method has been developed which rests on the use of chick embryo fibroblasts of strain Leghorn Spafas C/0. These cells are sensitive to all the avian retroviral subgroups.

In practice, secondary fibroblasts in culture are infected with increasing dilutions of virus suspension and then cultured in the presence of G418. The titre of the virus in r-ffu/ml (resistant focus forming unit) represents the product of the number of resistant foci per culture multiplied by the dilution of the viral suspension used for the infection.

A critical point of this test is the time of addition of the drug relative to the time of infection. The addition of the drug must not be excessively delayed, in order to avoid secondary infections which would lead to an overestimation of the titre of the virus, nor must it be too early in order to enable the Neo$^r$ protein to be expressed in sufficient quantity in the infected cells for the latter to be rendered resistant.

Kinetic analysis shows that the estimation of the titre by this test is identical when the drug is added during the 24 hours which follow the infection. The dose of G418 used for the Spafas chick fibroblasts is 200 μg/ml.

The vectors according to the present invention enable cells resistant to G418 to be prepared, and have made it possible to clone and express human globin, especially human delta-globin, the experiments on the other globins having given equivalent results.

EXAMPLE 18

DEVELOPMENT OF AVIAN HELPER CELLS

This example relates to cultures of avian helper cells in which the 3 genes gag, pol and env are expressed but are unable to be encapsidated in the virions produced.

The assembly of the gag-pol-env genes was isolated in a single DNA fragment from a plasmid containing the genome of the RAV-1 helper virus supplied by J. M. Bishop (UCSF). This fragment is bounded on the 5' side by a SacI site situated 146 nucleotides upstream of the initiator codon of the gag gene, and on the 3' side by an AccI site situated 120 nucleotides downstream of the termination codon of the env gene. The sequences responsible for encapsidation of the avian viral genomes are not present in the fragment in question. This fragment was inserted in plasmids which enabled the expression of genes to take place in eukaryotic cells.

In plasmid HP1, the gag-pol-env assembly was cloned between the TK gene promoter of the HSVI virus and the polyadenylation signal of the same virus, both isolated from the plasmid pAG 60 of Colbere-Garapin et al. (1981).

In plasmid HP2, the gag-pol-env genes were inserted between the promoter-enhancer of the SV40 virus early gene and a sequence containing the intron of the t gene and the polyadenylation signal of SV40 virus, all isolated from the plasmid pSv2gpt of Mulligan and Berg (1981).

These plasmids were transfected into quail cells, line QT6, and chick fibroblasts. In order to select the transfected cells, the DNA of these plasmids was cotransfected with the DNA of plasmids carrying a selection marker, either plasmid pAG60 or plasmid pXJ12. The cell foci resistant after selection with G418 were withdrawn and cultured separately. Others were combined and cultured as a mixture. The production of viral particles by these cells was tested by looking for the presence of reverse transcriptase in particulate form in the culture supernatants. This activity was compared to that of the supernatants of chick 6C$_2$ erythroleukaemic cells which are highly productive of AEV virus. Of 9 QT6 cell cultures transfected with HP1 and HP2, 7 show significant reverse transcriptase activity, of which 5 show activity greater than that of 6C2 cells.

These results show:

on the one hand, that it is possible for the gag, pol and env genes to be expressed from a promotor other than that present in the viral LTR sequences, on the other hand, that it is possible to produce extracellular virions from helper viral genomes devoid of LTR and encapsulation sequences.

FILING OF STRAINS

The following strains have been filed on 9th Oct. 1985 with the Collection Nationale de Cultures de Microorganismes de L'Institut Pasteur (National Collection of Microorganism Cultures of the Institut Pasteur), 28, rue du Docteur-Roux, 75724 PARIS, CEDEX 15, under the following numbers:

| Strain E. coli 600 pAEV TSN | No. I-492 |
| Strain E. coli 600 RS pAEV 28 | No. I-493 |
| Strain E. coli 600 RS pAEVXJ12 | No. I-494 |

REFERENCES

BECK E., LUDWIG C., AUERSWALD E.A., REISS B. and SCHALLER H. (1982). Nucleotide sequence and exact location of the neomycin. Gene 19 : 327-336.

KAWAI S. and NISHIZAWA M. (1984). New procedure for DNA transfection with polycation and dimethyl sulfoxide. Mol. Cell. Biol. 4 : 1172-1174.

MESSING J. and VICIRA J. (1982). A new pair of M13 vectors for selecting either DNA strand of double-digest restriction fragments. Gene 19 : 269-276.

SANGER F., NICKLEN S.and COULSON A.R. (1977). DNA sequencing with chain terminating inhibitors. Proc. Natl. Acad. Sci. 74 : 5463-5467.

SHARP P.A. (1981). Speculation on RNA splicing. Cell 23 : 643-646.

AUFFRAY C. and ROUGEON F. (1980). Purification of Mouse Immunoglobulin Heavy Chain Messenger. RNAs from Total Myeloma Tumor RNA. Eur. J. Biochem. 107 : 303-314.

BIRNBOIM H. C. and DOLY J. (1979). A rapid alkaline extraction procedure for screening recombinant plasmid DNA. Nucl. Acid. Res. 7 : 1513-1523.

BOONE L. R. and SKALKA A. M. (1981). Viral DNA Synthetized in vitro by Avian Retrovirus Particles Permeabilized with Melittin. J. Virology 37 (1) 117-126.

COLBERE-GARAPIN F., HORODNICEANU F., KOURILSKY P. and COLBERE-GARAPIN A. (1981). A new Dominant Hybrid Selectable Marker for Higher (ukaryotic Cells. J. Mol. Biol. 150 : 1-14.

CULLEN B. R., LOMEDICO P. T. and JU G. (1984). Transcriptional Interference in Avian Retroviruses Implication for the promoter Insertion Model of Leukemogenesis. Nature 307 : 241-245.

EL-GEWELY M. R. and HELLING R. B. (1980). Preparative Separation of DNA Ethidium Bromide Complexes Zonal Density Gradient Centrifugation. Anal. Biochem. 102 : 423-428.

GRAHAM F. L. and VAN DER EB A. T. (1973). A new Technique for the Assay of Infectivity of Human Adenovirus 5 DNA. Virology 52 : 456-467.

LEHRACH H., DIAMON D., WOZNEY J. M. and BOEDTKER H. (1977). RNA Molecular Weight Determination by Gel Electrophoresis under Denaturing Conditions a Critical Reexamination. Biochem 16 : 4763-4751.

LONGACRE S. S. and RUTTER W. (1977). Isolation of Specific DNA Sequences by Sulphydryl Sepharose Chromatography of Mercurated Polynucleotides. J. Biol. Chem. 252 : 2742-2752.

MANIATIS T., FRITSH E. F. and SAMBROOCK J. (1982). Molecular Cloning. A Laboratory Manual ( Cold Spring Harbor NEW-YORK: Cold Spring Harbor Laboratory).

McMASTER M. and CARMICHAEL G. G. (1977). Analysis of Single and Double stranted Nucleic Acids on Polyacrylamide and Agarose Gels by Using Glyoxal and Acridine Orange. Proc. Natl. Acad. Sci. USA 74 : 4835-4838.

MILLER A. D., JOLLY D. J., FRIEDMAN T. and VERMA. M (1983). A Transmissible Retrovirus Expressiong Human Hypoxanthine Phosphoribosyl transferase (HPRT) : Gene Transfer into Cells Obtained from Human Deficient in HPRT. Proc. Natl. Acad. Sci. USA 80 : 4709-4713.

PONCZ M., SCHWARTZ E., BALLATINE M. and SURREY S., (1983). Nucleotide Sequence Analysis of the delta beta Globin Gene Region in Human. J. Biol. Chem. 258 : 11599-11609.

RIGBY P. W. J., DIEKMAN M., RHODES C. and BERG P. (1977). Labelling Deoxyribonucleic Acid to High Specific Activity in vitro by Nick Translation with DNA Polymerase. J. Mol. Biol. 113 : 237-251.

SOUTHERN E. M. (1975). Detection of Specific Sequence Among DNA Fragments Separated by Gel Electrophoresis. J. Mol. Biol. 98 : 503-517.

TAUTZ D. and RENZ M. (1983). An Optimized Freeze-Squeeze Method for the Recovery of DNA Fragments from Agarose Gels. Anal. Biochem. 132 : 14-19.

THOMAS P.S. (1980). Hybridation of Denatured RNA and Small DNA Fragments Transfered to Nitrocellulose. Proc. Natl. Acad. Sci. USA 77 (9) : 5201-5209.

VENNSTROM B., FANSHIR L., MOSCOVICI C.and BISHOP J. M. (1980). Molecular Cloning of the Erythroblastosis virus Genome and Recovery of Oncogenic Virus by Transfection of Chicken Cells. J. Virol. 36 : 575-587.

WIGLER M., SILVERSTEIN S., LEE L. S., PELLICER A., CHENG Y. C. andAXEL R. (1977). Transfer of Purified Herpes Virus Thymidine Kinase Gene to Cultures Cells. Cell 11 : 223-232.

YAMAMOTO T., NISHIDA T., MIYAJIMA N., KAWAI S., OOI T. and TOYOSHIMA K. (1983). The erbB gene of Avian Erythroblastosis Virus is a Member of the src Gene Family. Cell 35 : 71-78.

SANGER F., WICKLEN J., COULSON A.R. (1977). DNA sequencing with chain terminating inhibitors, Proc. Natl. Acad. Sci. USA 74, 5463-5467.

SORGE J., WRIGHT D., ERDMAN V. D., CUTTING A. E. (1983). Amphotropic retrovirus vector system for human cell gene transfert. Mol. Cell. Biol. 4, 1730-1737.

YAMAMOTO T., HINARA H., NISHIDA T., KAWAI S., TAYASHIMA K. (1983). A new avian erythroblastosis virus AEV-H carries erb-B gene responsible for the induction of both erythroblastosis and sarcomas. Cell 34, 225-232.

BIGGIN M. D., GIBSON T. J., HONG G. F. (1983). Buffer gradient gels and 35S label as aid to rapid DNA sequence determination. Proc. Natl. Acad. Sci. USA 80, 3963-3965.

BOLIVAR F., RODRIGUEZ R. L., GREEN P. J., BETLACH M. C., HEYNECKER H. L., BOYER H. W., CROSA J. H., FALKOW S. (1977). Construction and characterization of new cloning vehicules. A multiple purpose cloning system. Gene 2, 95-113.

DEBUIRE B., HENRY C., BENAISSA M., BISERTE G., CLAVERIE J. M., SAULE S., MARTIN P., STEHELIN D. (1984). Sequencing the erb-A gene of avian erythroblastosis virus reveals a new type of oncogene. Science 224, 1456-1459.

DENTE L., CESARENT G., CORTESE R. (1983). pEMBL: a new family of single stranded plasmids. Nucl. Acids Res. 11, 1645-1655.

We claim:

1. An infectious virus for cloning or expression of a foreign gene, wherein said virus comprises all or part of the genome of an avian erythroblastosis virus, two LTR sequences from said avian retrovirus genome, at least one foreign gene situated between said LTR sequences, and two mRNA splicing sites.

2. A virus according to claim 1 wherein said virus possesses transforming activity.

3. A virus according to claim 2 wherein said foreign gene is inserted between the v-erbB gene and the downstream LTR.

4. A virus according to claim 1 wherein said foreign gene is joined to the transcriptional and translational control sequences of a gene from said retrovirus.

5. A virus according to claim 4 wherein said virus is the virus AE2LTR.

6. A virus according to claim 1 wherein said virus lacks transforming activity.

7. A virus according to claim 6 wherein the v-erbB gene has been at least partially deleted.

8. A virus according to claim 6 wherein at least one foreign gene is inserted downstream of the v-erbA gene.

9. A virus according to claim 6 wherein said virus does not contain v-erbA and v-erbB.

10. A virus according to claim 9 wherein two foreign genes are inserted between the two LTR sequences of said virus.

11. A virus according to claim 10 wherein one of the two said foreign genes is inserted between the two splicing sites, and the other foreign gene is inserted downstream from the 3' splicing site.

12. A virus according to claim 10 wherein one of the two said foreign genes encodes a selectable marker.

13. A virus according to claim 10 wherein at least one inserted foreign gene is selected from the group consisting of: (1) The human delta-globin gene, (2) The human beta-globin gene, (3) The human alpha-globin gene, and (4) A bacterial neomycin resistant gene.

14. A virus according to claim 1, wherein said foreign gene or genes comprise transcriptional and translational control sequences capable of functioning in a eukaryotic cell.

15. A virus according to claim 10 wherein said virus comprises at least the unique restriction site located between the two splicing sites, and at least one unique restriction site downstream from the splicing sites.

16. A virus according to claim 15 wherein the unique restriction site located downstream from the splicing sites is an NdeI recognition site comprising a translation initiation codon.

17. A plasmid vector comprising a cDNA copy of the virus according to claim 1.

18. A plasmid vector according to claim 17 wherein said plasmid comprises the DNA sequence of a bacterial plasmid, a phage or a cosmid.

19. A plasmid vector according to claim 18 wherein said plasmid vector comprises at least one marker for selection in bacteria.

* * * * *

UNITED STATES PATENT AND TRADEMARK OFFICE
CERTIFICATE OF CORRECTION

PATENT NO. : 4,957,865

DATED : September 18, 1990

INVENTOR(S) : Jacques Samarut et al

It is certified that error appears in the above-identified patent and that said Letters Patent is hereby corrected as shown below:

COLUMN 14;

Claim 5, line 2, change "AE2LTR" to --AEV2LTR--.

Signed and Sealed this

Thirteenth Day of October, 1992

*Attest:*

DOUGLAS B. COMER

*Attesting Officer*  *Acting Commissioner of Patents and Trademarks*